(12) United States Patent
McDermott et al.

(10) Patent No.: US 9,260,411 B2
(45) Date of Patent: Feb. 16, 2016

(54) SYNTHESIS OF (2S,5R)-5-ETHYNYL-1-{N-(4-METHYL-1-(4-CARBOXY-PYRIDIN-2-YL)-PIPERIDIN-4-YL)GLYCYL}PYRROLIDINE-2-CARBONITRILE

(75) Inventors: Todd S. McDermott, Libertyville, IL (US); Seble H. Wagaw, Evanston, IL (US); Kenneth M. Engstrom, Mundelein, IL (US); Jorge Gandarilla, North Riverside, IL (US); Albert Kruger, Pleasant Prairie, WI (US); Michael J. Rozema, Kenosha, WI (US); Michael G. Fickes, Evanston, IL (US); Steven J. Wittenberger, Mundelein, IL (US); Lakshmi Bhagavatula, Vernon Hills, IL (US); Thomas B. Borchardt, Kenosha, WI (US)

(73) Assignee: AbbVie Inc., North Chicago, IL (US)

( * ) Notice: Subject to any disclaimer, the term of this patent is extended or adjusted under 35 U.S.C. 154(b) by 1598 days.

(21) Appl. No.: 11/779,936

(22) Filed: Jul. 19, 2007

(65) Prior Publication Data

US 2008/0058528 A1 Mar. 6, 2008

Related U.S. Application Data

(60) Provisional application No. 60/807,901, filed on Jul. 20, 2006.

(51) Int. Cl.
*C07D 401/14* (2006.01)
*C07D 401/04* (2006.01)

(52) U.S. Cl.
CPC ............ *C07D 401/14* (2013.01); *C07D 401/04* (2013.01)

(58) Field of Classification Search
CPC ... C07D 401/06; C07D 401/12; C07D 401/14
USPC .................................................. 546/193, 208
See application file for complete search history.

(56) References Cited

U.S. PATENT DOCUMENTS

| 4,923,983 | A * | 5/1990 | Wright | 540/363 |
| 7,238,724 | B2 * | 7/2007 | Madar et al. | 514/422 |
| 7,262,207 | B2 * | 8/2007 | Madar et al. | 514/326 |
| 2004/0121964 | A1 | 6/2004 | Madar et al. | 514/326 |
| 2005/0215784 | A1 | 9/2005 | Madar et al. | 514/326 |

FOREIGN PATENT DOCUMENTS

JP 10072440 3/1998

OTHER PUBLICATIONS

Mader et al. "Preparation of N-aminoacyl . . . " Ca 140:303518 (2004).*
Madar et al. "Preparation of cyanopyrrolidine . . . " CA143:347048 (2005).*
Medical Dictionary "partition chromatography" p. 1 (2013).*
Madar et al. "Preparation of cyanopyroolidine . . . " CA143:347048 (2005).*
Berge et al. "Pharmaceutical salt" J. Pharm. Sci. 66(1) 1-19 (1977).*
Granados-Correa "The ball miling effect . . . " J. Chil. Chem. Sco. 54(3) 252-255 (2009).*
Manfre, et al., "Synthesis of Proline Analogues as Potential Mechanism Based Inhibitors of Proline Dehydrogenase: 4-Methylene-L-(E) and (Z)-4-(Fluoromethylene)-cis and trans-5-Ethynyl (+−), and cis- and trans-5-Vinyl-L-Proline," Journal of Organic Chemistry 57(7): 2060-2065 (1992).
Pei, et al., "Discovery, Structure-Activity relationship, and Pharmacological Evaluation of (5-Substituted-pyrrolidinyl-2-carbonyl)-2-cyanopyrrolidines as Potent Dipepotidyl Peptidase IV Inhibitors," Journal of Medicinal Chemistry, 49(12): 3520-3535 (2006).
Madar, et al., "Discovery of 2-[4-{{2-(2S, 5R)-2-Cyano-5-ethynyl-1-pyrrolidinyl]-2-2-oxethyl]amino]-4-methyl-1-piperidinyl]-4-pyridinecarboxylic Acid (ABT-279)," Journal of Medicinal Chemistry, 49(21): 6416-6420 (2006).
Wade, L.G., Jr., Organic Chemistry, 3rd ed., Chapter 19 entitled "Amines," p. 879-884; Chapter 21 entitled "Carboxylic Acid Derivatives," p. 987, Dec. 22, 1994.

* cited by examiner

*Primary Examiner* — Celia Chang
(74) *Attorney, Agent, or Firm* — Lisa V. Mueller; Michael Best & Friedrich LLP

(57) ABSTRACT

A process for making (2S,5R)-5-ethynyl-1-{N-(4-methyl-1-(4-carboxy-pyridin-2-yl)piperidin-4-yl)glycyl}pyrrolidine-2-carbonitrile and salts thereof, and intermediates used in the process are disclosed.

8 Claims, No Drawings

SYNTHESIS OF (2S,5R)-5-ETHYNYL-1-{N-(4-METHYL-1-(4-CARBOXY-PYRIDIN-2-YL)-PIPERIDIN-4-YL)GLYCYL}PYRROLIDINE-2-CARBONITRILE

CROSS-REFERENCE SECTION TO RELATED APPLICATIONS

This application claims the benefit of U.S. Provisional Patent Application No. 60/807,901, filed Jul. 20, 2006, which is hereby incorporated by reference in its entirety.

TECHNICAL FIELD

The invention relates to a process for the preparation of (2S,5R)-5-ethynyl-1-{N-(4-methyl-1-(4-carboxy-pyridin-2-yl)piperidin-4-yl)glycyl}pyrrolidine-2-carbonitrile, having the following structure (formula I):

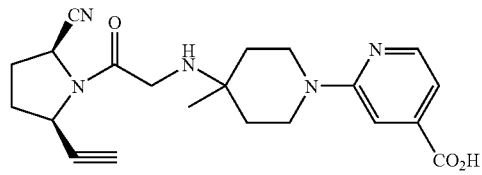

or salts thereof, intermediates for producing thereof and processes for producing the intermediates.

BACKGROUND OF THE INVENTION (2S,5R)-5-ethynyl-1-{N-(4-methyl-1-(4-carboxy-pyridin-2-yl)piperidin-4-yl)glycyl}pyrrolidine-2-carbonitrile (formula I) has been reported as inhibitor of DPP-IV. As a result, it is useful in the treatment of disorders mediated by DPP-IV such as, but not limited to, diabetes, type II diabetes, hyperglycemia, Syndrome X, hyperinsulinemia and obesity.

The synthetic route that was used to prepare the trifluoroacetic acid salt of (2S,5R)-5-ethynyl-1-{N-(4-methyl-1-(4-carboxy-pyridin-2-yl)piperidin-4-yl)glycyl}pyrrolidine-2-carbonitrile as disclosed in U.S. Patent Application Publication Number US2004/0121964, is outlined in Scheme 1 below. Specifically, the synthesis includes reaction of an acid of formula (II) with triphenyl phosphine and diphenylphosphoryl azide provided carbamate of formula (III), which was treated with HCl in dioxane to provide amine of formula (IV). A refluxed solution of 2-fluoroisonicotic acid (formula (V)) in benzene and 2-methyl-propan-2-ol was treated with N,N-dimethylformamide di-tert-butyl acetal to provide a protected acid of formula (VI). Displacement of the fluorine atom of formula (VI) with amine of formula (IV) occurred, followed by treatment with ammonium formate in the presence of 10% palladium on carbon at elevated temperature provided amine of formula (VIII). Treatment of methyl (S)-(+)-2-pyrrolidone-5-carboxylate with methyl chloroformate in the presence of lithium bis(trimethylsilyl) amide provided the corresponding methyl carbamate of formula (IX). Reduction of the compound of formula (IX) with lithium triethylborohydride occurred, followed by treatment with methanol in the presence of p-toluenesulfonic acid hydrate provided ether of formula (X). Treatment of the ether with bistrimethylsilylacetylene, tin(IV) chloride and aluminum chloride was followed by separation of the diastereomers using column chromatography gave the desired diastereomer of formula (XI). Treatment of compound of formula (XI) with iodotrimethylsilane afforded the deprotected L-pyrolidnate of formula (XII). Reaction of compound of formula (XII) with chloroacetyl chloride provided 1-chloroacetyl-L-prolinate of formula (XIII). Hydrolysis of the compound of formula (XIII) with lithium hydroxide provided an acid of formula (XIV). Acid of formula (XIV) was treated with isobutyl chloroformate in the presence of 4-methylmorpholine, and the resulting intermediate was treated with a solution of ammonia in dioxane to provide amide of formula (XV). Dehydration of amide of formula (XV) with phosphoryl chloride in the presence of imidazole and pyridine provided the compound of formula (XVI). Displacement of the chloride of formula (XVI) with the amine of formula (VIII) was followed by purification using column chromatography provided compound of formula (XVII). Treatment of compound of formula (XVII) with trifluoroacetic acid in dichloromethane produced the trifluoroacetic acid salt of compound of formula (I).

Scheme 1

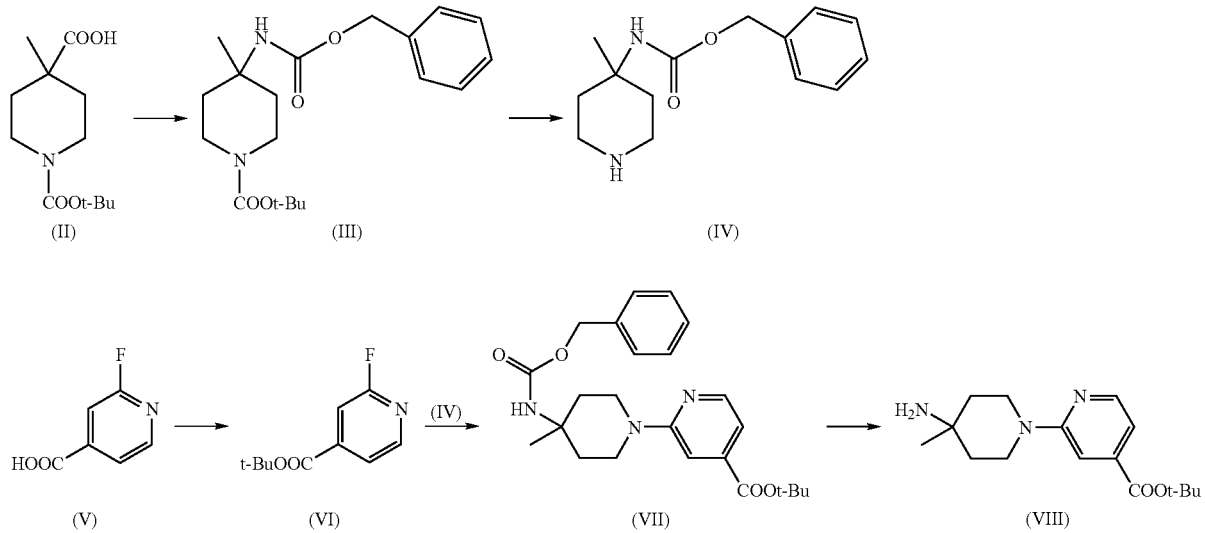

-continued

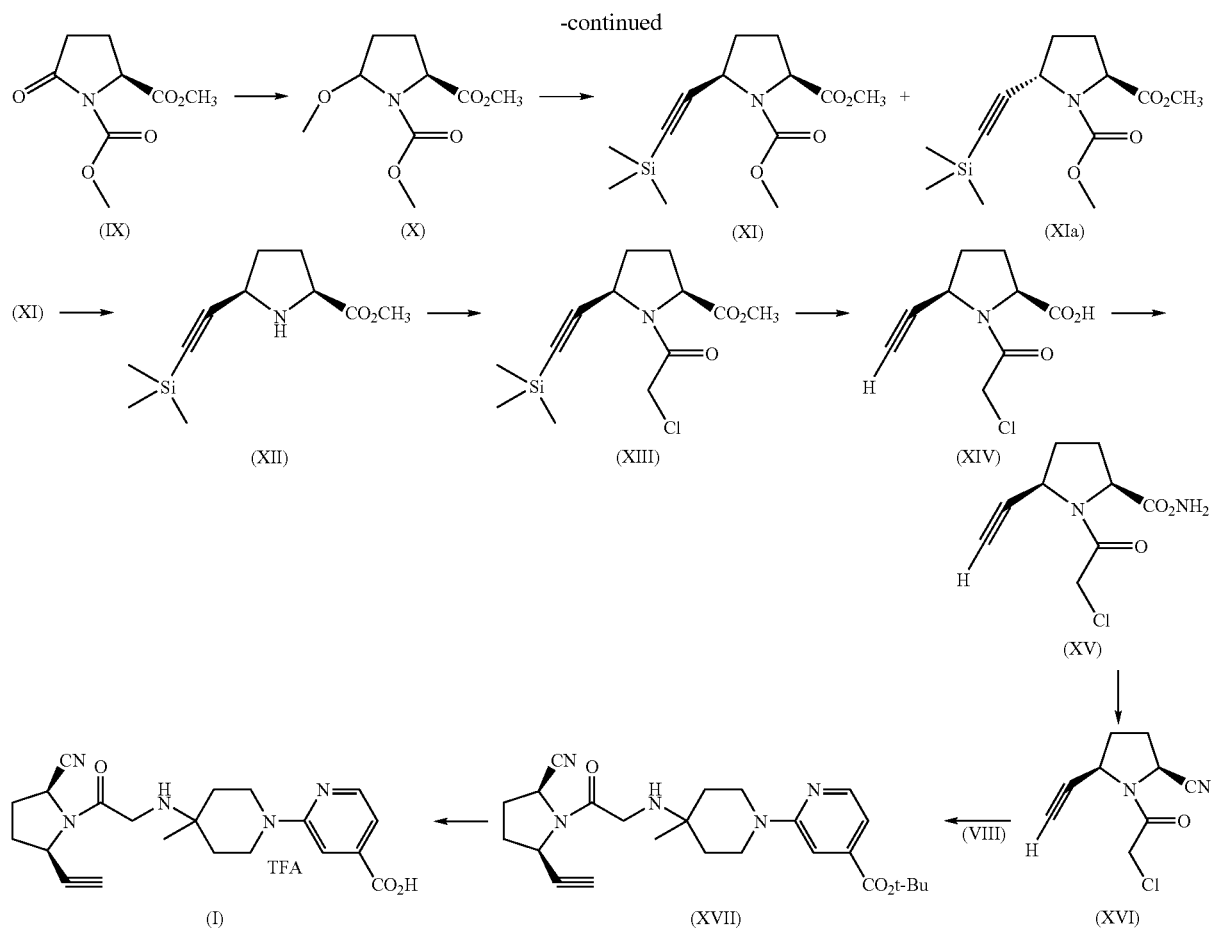

The above procedure entails formation of two diastereomeric intermediates (XI) and (XIa) and the requirement of chromatographic purification to obtain the desired diastereomer (XI). In addition, displacement of the chloride of formula (XVI) with amine of formula (VIII) was conducted in an aqueous dioxane environment at room temperature. Combination of these two operations resulted in low overall yield of the process. Therefore, the synthetic method outlined above is not suitable for large-scale preparation of the compound of formula (I) or salts thereof.

SUMMARY OF THE INVENTION

The present invention is directed to a novel process for the preparation of (2S,5R)-5-ethynyl-1-{N-(4-methyl-1-(4-carboxy-pyridin-2-yl)piperidin-4-yl)glycyl}pyrrolidine-2-carbonitrile of formula (I), or salts thereof. This process involves formation of a single diastereomeric intermediate and requires no chromatographic purification.

One aspect of the invention is directed to a process for preparing a compound of formula (I);

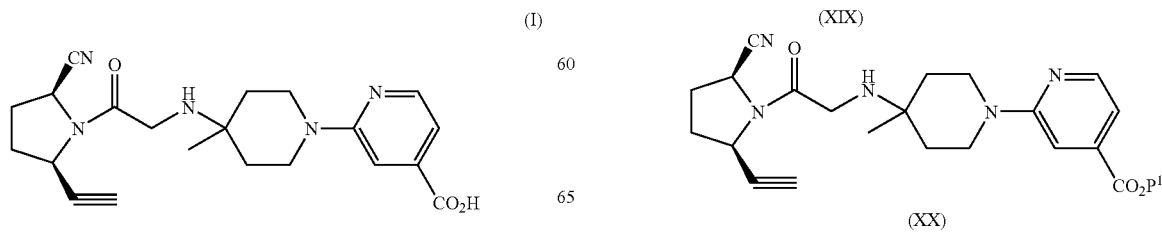

(I)

or a pharmaceutically acceptable salt thereof.

The process includes the following steps:

(a) reacting a compound of formula (XVIII) wherein $X^2$ is Cl, Br, I, methanesulfonate or p-toluenesulfonate, with a compound of formula (XIX) or salts thereof, wherein $P^1$ is an acid protecting group, an additive, and a base, in a solvent, to provide a compound of formula (XX);

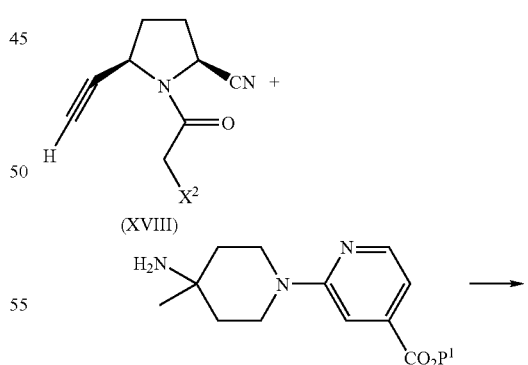

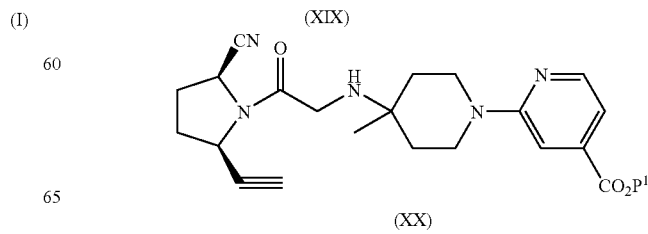

(b) optionally treating the compound of formula (XX) with an acid to provide a salt of the compound of formula (XX);

(c) deprotecting the compound of formula (XX) or salts thereof to provide a compound of formula (I).

The compound of formula (I) can be converted to an acid addition salt using any conventional techniques known in the art. Accordingly, another aspect of the invention is directed to the process for preparing the acid addition salt, particularly the L-malic acid salt of the compound of formula (I). Further, the present invention relates to certain intermediate compounds, or a salt thereof, that are made within the process of making the compound of formula (I). Moreover, the present invention relates to processes and alternative processes for preparing various intermediates thereof.

DETAILED DESCRIPTION OF THE INVENTION

Terms not specifically defined herein are given the meanings that would be given to them by one of skill in the art in light of the disclosure and the context.

As used above, and throughout the specification, the following terms, unless otherwise indicated, shall be understood to have the following meanings:

The term "$C_{1-10}$ alkyl", by itself or as part of other groups, means branched and unbranched hydrocarbon chain containing from 1 to 10 carbon atoms, while the terms "$C_{1-4}$ alkyl", "$C_{1-5}$ alkyl" and "$C_{1-6}$ alkyl", by themselves or as part of other groups, means branched and unbranched hydrocarbon chain containing from 1 to 4, 1 to 5 and 1 to 6 carbon atoms respectively. Non-limiting examples of alkyls include methyl, ethyl, n-propyl, isopropyl, n-butyl, iso-butyl, sec-butyl, tert-butyl, n-pentyl, iso-pentyl, neo-pentyl, hexyl, n-heptyl, n-octyl, n-nonyl, and n-decyl.

The term "$C_{1-6}$ alcohol" means $C_{1-6}$ alkyls wherein one or two hydrogen atoms are substituted by —OH radicals. Accordingly, the term "$C_{1-4}$ alcohol" means $C_{1-4}$ alkyls wherein one or two hydrogen atoms are substituted by OH radicals. Preferred are allyl groups with one to four carbon atoms. Non-limiting examples include: methanol, ethanol, n-propanol, isopropanol, n-butanol, iso-butanol, sec-butanol, tert-butanol, n-pentanol, isopentanol, neo-pentanol or hexanol. Unless otherwise indicated, the terms propanol, butanol, pentanol, and hexanol include all possible isomeric forms of the groups in question. Thus, for example, propanol includes n-propanol, and isopropanol, butanol includes iso-butanol, sec-butanol and tert-butanol.

The term "$C_{1-6}$ carboxylic acid" means a $C_{1-6}$ alkyl group as defined herein wherein one of the hydrogen atoms is replaced by COOH. Non-limiting examples of $C_{1-6}$ carboxylic acids include: acetic acid, propanoic acid, butanoic acid, pentanoic acid and hexanoic acid.

The term "$C_{1-6}$ alkoxy", by itself or used with other groups, means a $C_{1-6}$ alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The present invention has numerous embodiments. In one embodiment, the present invention is directed towards a novel process for the preparation of (2S,5R)-5-ethynyl-1-{N-(4-methyl-1-(4-carboxy-pyridin-2-yl)piperidin-4-yl)glycyl}pyrrolidine-2-carbonitrile of formula (I), or salts thereof. This process involves formation of a single diastereomeric intermediate and requires no chromatographic purification.

Another embodiment of the present invention is directed towards a process for preparing a compound of formula (I):

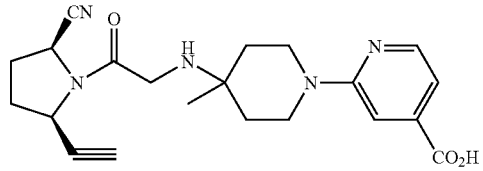

or a pharmaceutically acceptable salt thereof.

The process includes the following steps:

(a) reacting a compound of formula (XVIII) wherein $X^2$ is Cl, Br, I, methanesulfonate or p-toluenesulfonate, with a compound of formula (XIX) or salts thereof, wherein $P^1$ is an acid protecting group, an additive, and a base, in a solvent, to provide a compound of formula (XX);

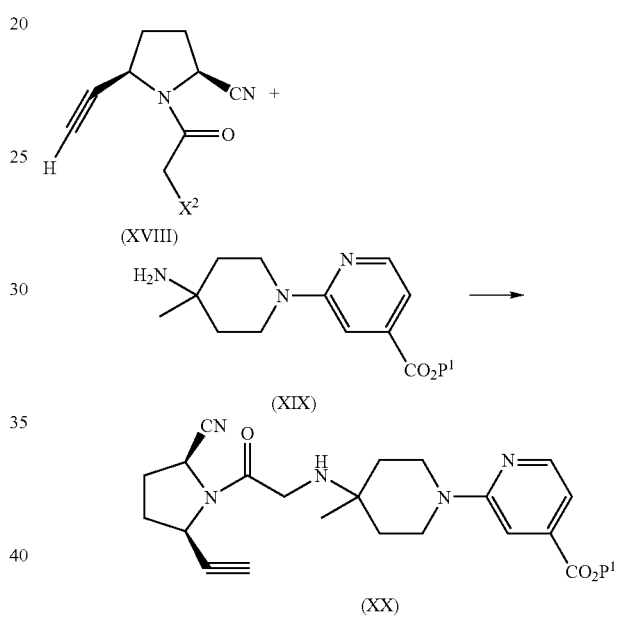

(b) optionally treating the compound of formula (XX) with an acid to provide a salt of the compound of formula (XX);

(c) deprotecting the compound of formula (XX) or salts thereof to provide a compound of formula (I).

The compound of formula (I) can be converted to an acid addition salt using any conventional techniques known in the art. Accordingly, another embodiment of the present invention is directed towards the process for preparing the acid addition salt, particularly the L-malic acid salt of the compound of formula (I).

A further embodiment of the present invention relates to certain intermediate compounds, or a salt thereof, that are made within the process of making the compound of formula (I). Accordingly, another embodiment of the present invention is directed towards a novel process for preparing the compound of formula (XIX) or salts thereof, wherein $P^1$ is an acid protecting group, or salts thereof.

The process includes the following steps:

(a) treating a compound of formula (XXIII) wherein $P^1$ is an acid protecting group and X is F, Cl, Br, I, methanesulfonate or p-toluenesulfonate, with amines of formula (XXII), or salts thereof, to provide a compound of formula (XXIV); and

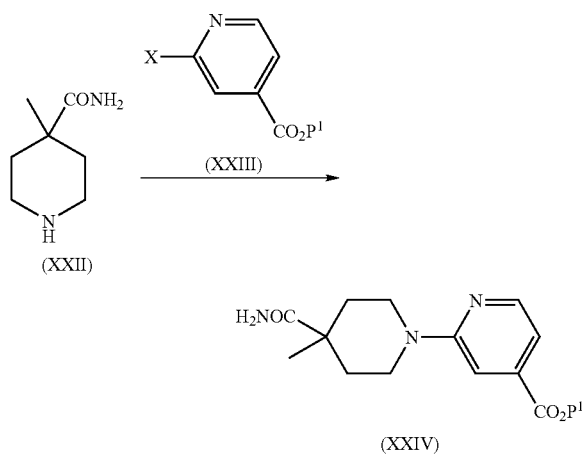

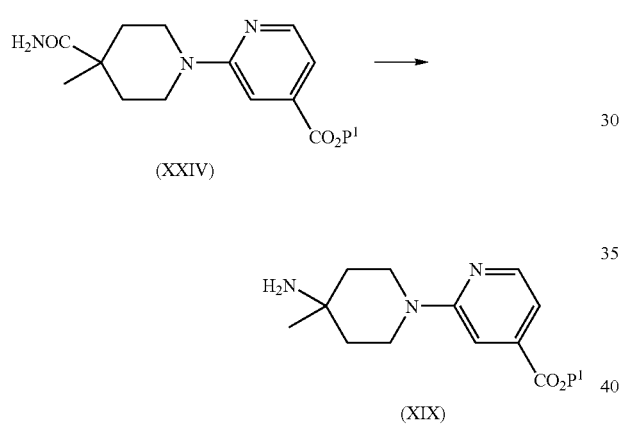

(b) treating the compound of formula (XXIV) with a halogenating reagent and a base to provide a compound of formula (XIX).

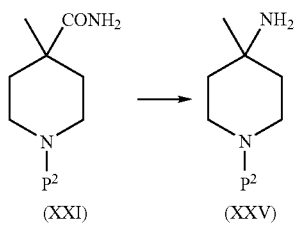

A further embodiment of the present invention is directed towards another process for preparing the compound of formula (XIX) wherein $P^1$ is an acid protecting group, or salts thereof.

The process includes the following steps of:

(a) treating a compound of formula (XXI) wherein $P^2$ is an amine-protecting group with a halogenating reagent and a base to provide a compound of formula (XXV);

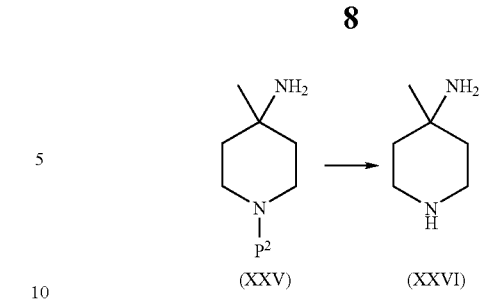

(b) deprotecting the compound of formula (XXV) or salts thereof to provide a compound of formula (XXVI), or salts thereof;

(c) treating a compound of formula (XXVII) or (XXIII) wherein $P^1$ is an acid protecting group, X is F, Br, Cl, I, methanesulfonate or p-toluenesulfonate and Y is F, Br, Cl or I, with the compound of formula (XXVI), or salts thereof, to provide a compound of formula (XXVIII) or (XIX) respectively;

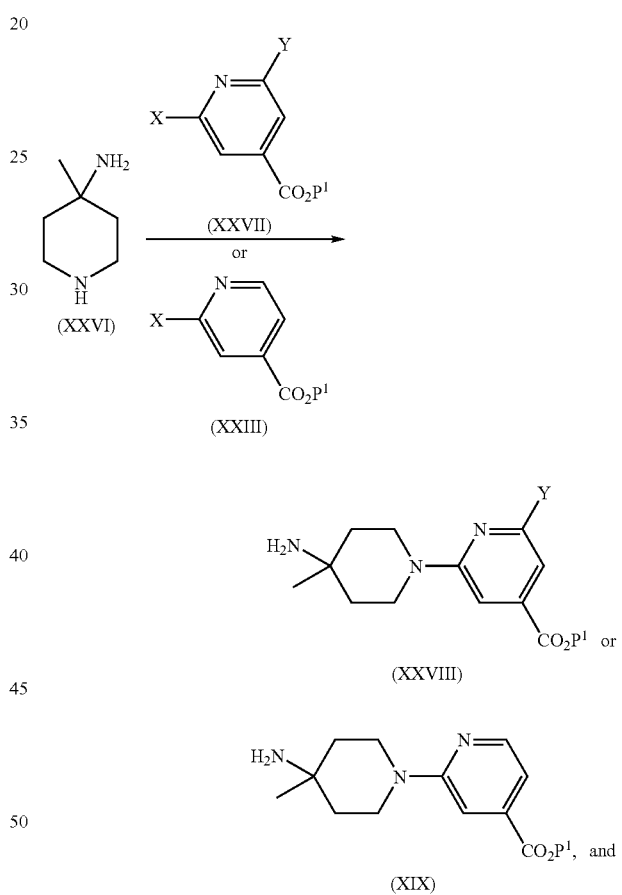

(d) de-halogenating the compound of formula (XXVIII) to provide the compound of formula (XIX)

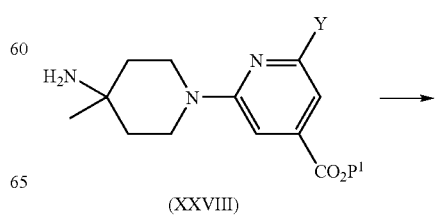

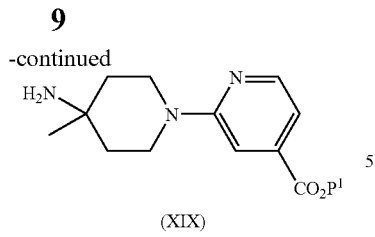

(XIX)

Yet another embodiment of the present invention is directed towards a process for preparing a compound of formula (XXVIIb) wherein $X^1$ is F, Cl, Br, I, methanesulfonate or p-toluenesulfonate and $Y^1$ is H, F, Cl, Br or I, by treating a compound of formula (XXVIIa) with ditert-butyl dicarbonate in the presence of 4-dimethylaminopyridine (DMAP).

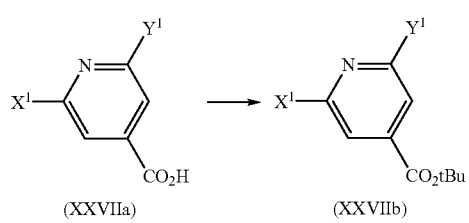

(XXVIIa)    (XXVIIb)

Another embodiment of the present invention is directed towards a process for preparing the compound of formula (XVIII) wherein $X^2$ is Cl or Br.

The process includes the steps of.

(a) treating a compound of formula (XXIX) wherein $P^2$ is an amine protecting group and $R^1$ is an acid protecting group, with a reagent having formula $(R^2)_3Si—CCMgX^3$ wherein $X^3$ is Cl, Br or I and $R^2$ is $C_{1-6}$ alkyl, to provide a compound of formula (XXX);

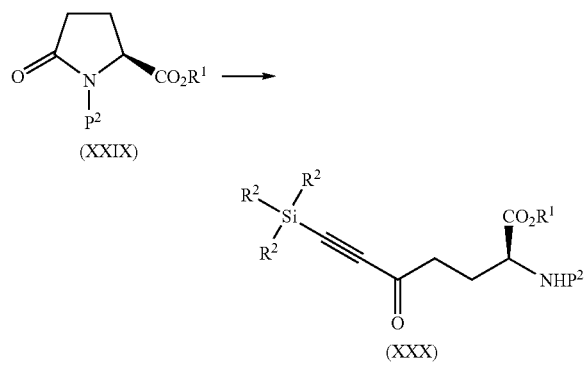

(XXIX)

(XXX)

(b) treating the compound of formula (XXX) with an acid and a reducing agent to provide a compound of formula (XXXI);

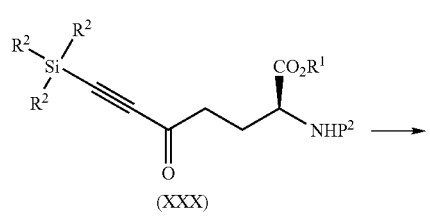

(XXX)

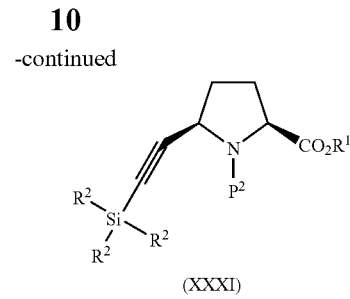

(XXXI)

(c) treating the compound of formula (XXXI) with a base, followed by treatment with an acid, to provide a compound of formula (XXXII);

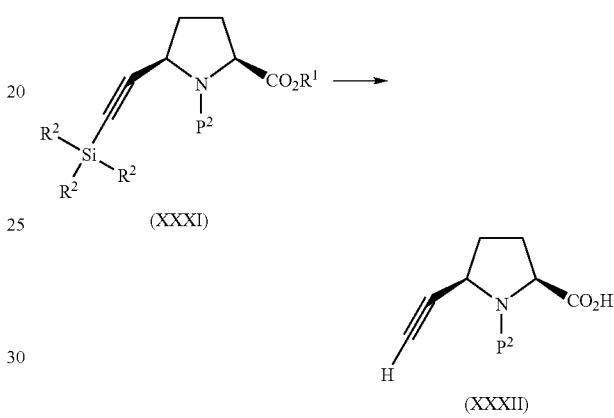

(XXXI)

(XXXII)

(d) treating the compound of formula (XXXII) with ammonia in the presence of a coupling reagent and a base, to provide a compound of formula (XXXIII);

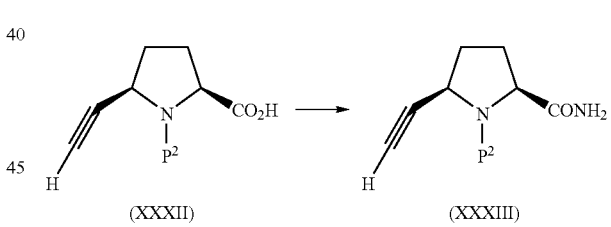

(XXXII)    (XXXIII)

(e) dehydrating the compound of formula (XXIII) to provide a compound of formula (XXXIV);

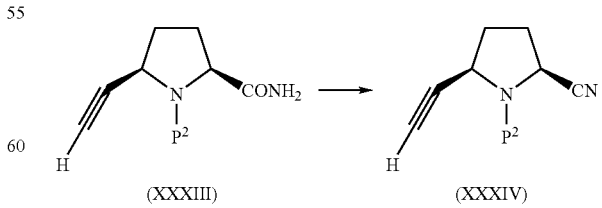

(XXXIII)    (XXXIV)

(f) deprotecting the compound of formula (XXXIV) to provide a compound of formula (XXXV) or salts thereof; and

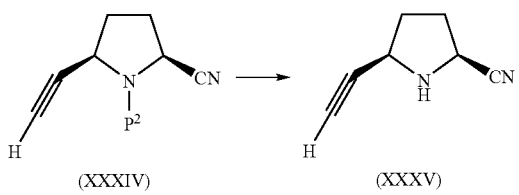

(g) treating the compound of formula (XXXV) or salts thereof with a reagent having formula $X^2CH_2COY^2$ wherein $X^2$ and $Y^2$ are independently Cl or Br, to provide a compound of formula (XVIII);

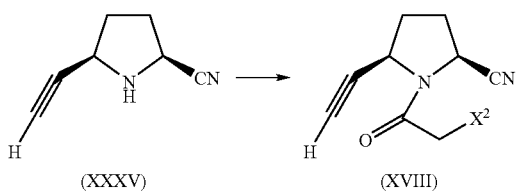

Still another embodiment of the present invention is directed towards a process for preparing a compound of formula (XXXVI), or a salt thereof, wherein $R^1$ is an acid protecting group and $R^2$ is $C_{1-6}$ alkyl

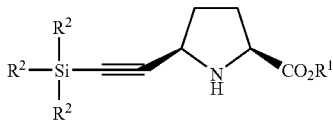

The process includes the steps of:

(a) asymmetric reduction of the compound of formula (XXX) wherein $P^2$ is an amine-protecting group, $R^1$ is an acid protecting group and $R^2$ is $C_{1-6}$ alkyl, to provide a compound of formula (XXXVII);

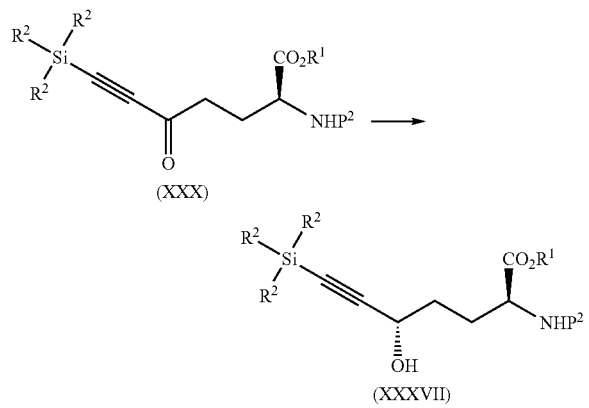

(b) activating the compound of formula (XXXVII) to provide a compound of formula (XXXVIII) wherein $R^4$ is trihaloacetyl, methanesulfonyl, benzenesulfonyl or p-toluenesulfonyl, without isolation; and

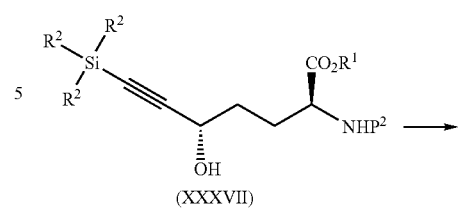

(c) deprotecting the amine-protecting group of the compound of formula (XXXVIII) followed by treatment with a base to provide a compound of formula (XXXVI) or salt thereof;

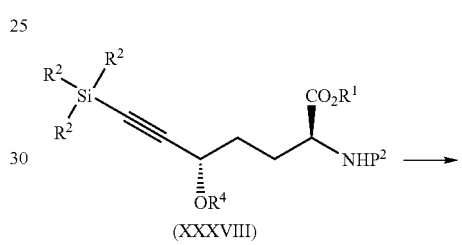

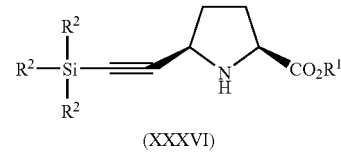

Yet another embodiment of the present invention is directed towards an alternative process for preparing a compound of formula (XVIII).

The process includes the steps of:

(a) saponifying a compound of formula (XXXVI) or salts thereof wherein $R^1$ is an acid protecting group and $R^2$ is $C_{1-6}$ alkyl, to provide a compound of formula (XXXIX);

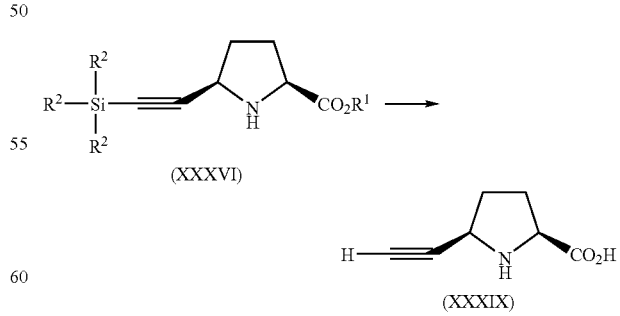

(b) treating the compound of formula (XXXIX) or salts thereof with a reagent having formula $X^2CH_2COY^2$ wherein $X^2$ and $Y^2$ are independently Cl or Br, to provide a compound of formula (XL);

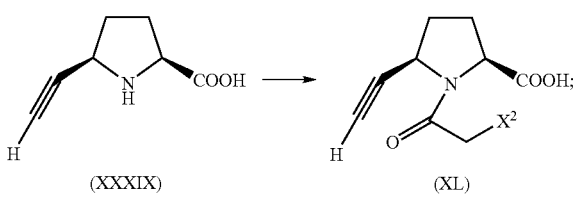

(c) treating the compound of formula (XL) with ammonia in the presence of a coupling reagent and a base, to provide a compound of formula (XLI); and

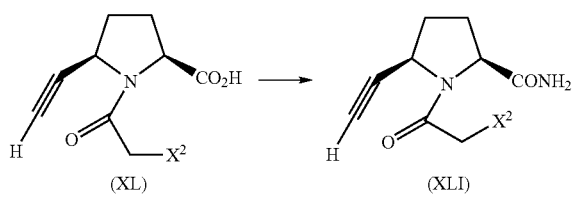

(d) dehydrating the compound of formula (XLI) to provide a compound of formula (XVIII).

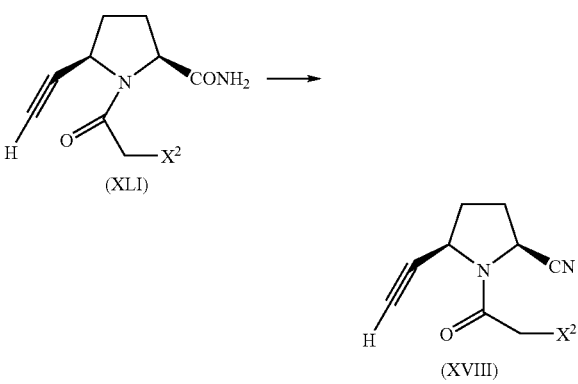

The final compound of formula (I) and intermediates used in the processes as disclosed herein can be converted to its pharmaceutically acceptable salts using any conventional techniques known in the art.

In any of the embodiments described herein, protection of any chemical functionality that cannot be compatible with the reaction conditions, and deprotection at suitable point in the reaction sequence of the method, are included in the scope of the invention. Suitable protecting groups and the methods for protecting and deprotecting different substituents using such suitable protecting groups are well know to those skilled in the art; examples of which can be found in T. Greene and P. Wuts, Protecting Groups in Chemical Synthesis (3$^{rd}$ ed), John Wiley & Sons, NY (1999), which is incorporated herein by reference in its entirety.

Examples of amine protecting groups suitable in the practice of the invention include allyl, methoxymethyl, benzyloxymethyl, $CY_3CO$ (where Y is Cl, Br, I or F), benzyloxycarbonyl, trityl, pivaloyloxymethyl, tetrahydranyl, benzyl, di(p-methoxyphenyl)methyl, triphenylmethyl, (p-methoxyphenyl)diphenylmethyl, diphenylphosphinyl, benzenesulfenyl, methyloxy carbonyl, 2-trimethylsilylethyloxy carbonyl, 1-methyl-1-phenylethyloxy carbonyl, tert-butoxy carbonyl (Boc), cyclobutyloxy carbonyl, 1-methylcyclobuty- loxy carbonyl, adamantyloxy carbonyl, vinyloxy carbonyl, allyloxy carbonyl, cinnamyloxy carbonyl 4,5-diphenyl-3-oxaline-2-one, benzyloxy carbonyl, 9-anthrylmethyloxy carbonyl, diphenylmethyloxy carbonyl and S-benzyloxy carbonyl.

Preferred amine protecting groups include methyloxy carbonyl, 2-trimethylsilylethyloxy carbonyl, 1-methyl-1-phenylethyloxy carbonyl, tert-butoxy carbonyl (Boc), cyclobutyloxy carbonyl, 1-methylcyclobutyloxy carbonyl, adamantyloxy carbonyl, vinyloxy carbonyl, allyloxy carbonyl, cinnamyloxy carbonyl 4,5-diphenyl-3-oxaline-2-one, benzyloxy carbonyl, 9-anthrylmethyloxy carbonyl, diphenylmethyloxy carbonyl and S-benzyloxy carbonyl, more preferably, tert-butoxy carbonyl (Boc).

Examples of acid protecting groups are esters, including $C_{1-6}$ alkyl esters, (unsubstituted or substituted with, for example $C_{1-6}$ alkoxy, $C_{1-6}$ alkylthio, $C_{1-6}$ alkoxy$C_{1-6}$ alkoxy, benzyloxy, trihalo, or $(C_{1-6}$ alkyl)$_3$silyl), allyl ester, and benzyl (unsubstituted or substituted with 2,4,6-trimethyl, p-nitro, o-nitro, p-bromo, p-methoxy, 2,6-dimethoxy) esters. Preferred acid protecting group are $C_{1-6}$ alkyl esters, particularly tert-butyl, methyl and ethyl esters.

Removal of the acid protecting group can be accomplished by catalytic hydrogenation, acidic or basic hydrolysis. Hydrogenation is generally carried out in oxygen free conditions, conveniently under inert gas, preferably under a hydrogen atmosphere. However, it is not essential for the reaction that the hydrogen for the hydrogenation be derived from the atmospheric gas. The hydrogen can also be produced in situ in solution from suitable hydrogen sources. Hydrogen sources of this kind include, for example, ammonium formate, formic acid and other formates, cyclodienes such cyclohexyldiene, and other hydrogen sources known in the art. The catalyst used is a metal catalyst such as palladium on carbon, platinum on carbon or palladium on alumina. Preferably, removal of the acid protecting group is achieved by acidic or basic hydrolysis, particularly basic hydrolysis.

The individual steps of the invention processes are described in detail below, along with other aspects of the present invention. The present invention includes not only the described multi-step process, but also the individual steps of the multi-step process and the various novel intermediates that are formed or used in such process steps.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Synthetic Examples section. Typically, reaction progress can be monitored by high-pressure liquid chromatography (HPLC) if desired. Reactions can be worked up in the conventional manner, e.g. by eliminating the solvent from the residue and further purified according to methodologies generally known in the art such as, but are not limited to, crystallization, distillation, extraction, trituration and chromatography. Un-less otherwise described, the starting materials and reagents are either commercially available or call be prepared by one skilled in the art from commercially available materials using methods described in the chemical literature.

It can be advantageous to carry out certain reaction processes under a protective gas atmosphere, preferably a nitrogen or argon atmosphere, or mixtures thereof.

The compounds according to the invention can be prepared according to the methods of synthesis described below, while the variables $R^1$, $R^2$, $R^3$, $R^4$, $P^1$ and $P^2$ have the above-mentioned meanings. These processes are to be understood as illustrating the invention without restricting the scope of the invention in any way.

Abbreviations used are: t-Bu for tert-butyl; EDCI for 1-ethyl-3-[3-(dimethylamino)propyl]-carbodiimide hydrochloride, DBU for 1,8-diazabicyclo[5.4.0]undec-7-ene, DMF for N,N-dimethylformamide, and HOBT for 1-hydroxybenzotriazole hydrate.

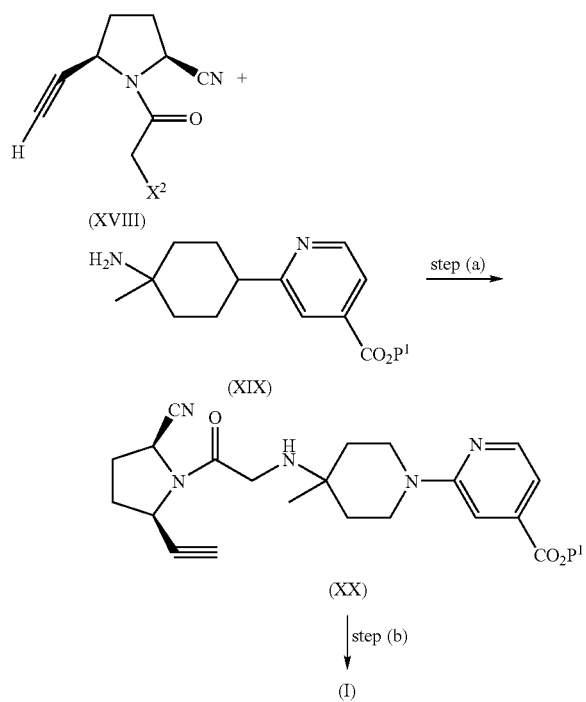

Scheme 2

Scheme 2 illustrates the preparation of the compound of formula (I) and salts thereof.

Step (a) includes reacting a compound of formula (XVIII) wherein $X^2$ is Cl, Br, I, methanesulfonate or p-toluenesulfonate, with a compound of formula (XIX) or salts thereof, wherein $P^1$ is an acid protecting group, a base, and with or without an additive, to provide a compound of formula (XX).

A similar process step wherein $X^2$ is Cl and $P^1$ is tert-butyl was described in U.S. Patent Application Publication Number US2004/0121964.

Process step (a) is improved by performing the reaction in an aprotic organic solvent, and in the presence of an additive, as compared to the use of dioxane and water as the solvent system and without an additive in the cited reference.

Step (a) is conducted by mixing a compound of formula (XIX) or salts thereof, wherein $P^1$ is an acid protecting group (preferably, $C_{1-6}$ alkyl and more preferably, tert-butyl), and an additive in a solvent, at a temperature ranging from about 20° C. to about 80° C., preferably from about 30° C. to about 45° C., more preferably from about 35° C. to about 40° C. Non-limiting examples of suitable bases that can be used include organic base and inorganic base. Suitable organic bases are tertiary amines such as tri($C_{1-6}$ alkyl)amines (e.g. triethylamine, diisopropylethyl amine, trimethylamine and the like), and tertiary cyclic amines (for example, N-methyl morpholine, DBU, 1,5-diazabicyclo-[4.3.0]non-5-ene, and the like), pyridine, and picolines. Suitable inorganic bases are metal salts or metal hydroxides (e.g. potassium, sodium or lithium hydroxides). Metal salts include metal carbonates (e.g. carbonates of sodium, potassium, barium and cesium), metal hydrogen carbonates (e.g. hydrogen carbonates of sodium, potassium, barium and cesium) and metal phosphates (e.g. phosphates of sodium and potassium). Preferably, metal phosphates are used. More particularly preferred is potassium phosphate. Even more particularly preferred is milled potassium phosphate. The base used is generally from about 1 to about 5 molar equivalents, with respect to the compound of formula (XIX), preferably from about 1 to about 2 molar equivalents, and more preferably from about 1 to about 1.5 molar equivalents. Non-limiting examples of solvents that can be used in step (a) are polar aprotic solvents such as acetonitrile, lactams (e.g. 1-methyl-2-pyrrolidinone), N,N-dimethylamides of formic acid and aliphatic $C_{1-6}$ carboxylic acids (e.g. N,N-dimethylformamide, N,N-dimethylacetamide, and the like), sulfoxides (e.g. dimethylsulfoxide), ethers (e.g. tetrahydrofuran, dioxane, diethyl ether, tert-butylmethyl ether, dimethoxyethane, and the like), aliphatic ketones (e.g. acetone, methyl ethyl ketone or methyl isobutyl ketone), and the like, and mixtures thereof. Particularly preferred are acetonitrile and lactams such as 1-methyl-2-pyrrolidinone N,N-dimethylformamide, N,N-dimethylacetamide, tetrahydrofuran and dioxane.

Examples of suitable additive include, but are not limited to, potassium iodide, sodium iodide, tetrabutylammonium iodide and lithium iodide. Preferred additive is potassium iodide. Preferably, the molar ratio of the additive to (XIX) is about 1:10 to about 1:5, more preferably, about 1:10.

After mixing, the temperature is raised to between about 25° C. and about 45° C., preferably to between about 30° C. and about 45° C., more preferably to between about 35° C. and about 40° C. About 1 to 1.5 molar equivalent of compound of formula (XVIII) (wherein $X^2$ is Cl, Br, I, methanesulfonate, or p-toluenesulfonate) with respect to compound of formula (XIX) is then added and the mixture is agitated for about 4 hours to about 18 hours, or until the reaction is complete. After this period of time, compound of formula (XX) is isolated. Optionally, compound of formula (XX), after isolation, can be treated with an acid, in a suitable solvent such as $C_{1-6}$ alcohols, preferably $C_{1-4}$ alcohols (e.g. methanol, ethanol, n-propanol, isopropanol and the like), and the solution was agitated for about 10 minutes to about 1 hour, preferably at about 15 minutes to about 30 minutes, at a temperature ranging from about 30° C. to about 70° C., preferably from about 60° C. to about 65° C. The mixture was then cooled to about 20° C. to about 25° C. and the acid salt of the compound of formula (XX) is then isolated by filtration. Non-limiting examples of acids that can be used include tartaric acid, D-tartaric acid, L-tartaric acid, malic acid, D-malic acid, L-malic acid, maleic acid, oxalic acid, S-mandelic acid and succinic acid. Preferred acids are D-tartaric acid and L-tartaric acid, more preferably D-tartaric acid.

Step (b) of the process as shown in Scheme 2 includes deprotection of the compound of formula (XX) or salts thereof to provide a compound of formula (I). A preferred method of deprotection is by treatment with an acid.

In U.S. Patent Application Publication Number US2004/121964, compound of formula (XX) wherein P¹ is tert-butyl was deprotected by stirring with trifluoroacetic acid in dichloromethane at ambient temperature, isolating the trifluoroacetic acid salt of compound of formula (I) by trituration with diethyl ether after completion of the reaction.

In step (b), to the compound of formula (XX) or salts thereof in a suitable solvent is added an acid. Non-limiting examples of acids that can be used include inorganic or organic acids such as ammonium sulfate, ammonium nitrate, hydrogen chloride (gaseous or in a solvent such as, but not limited to, water, dioxane, methanol, and acetic acid), sulfuric acid, phosphoric acid, trifluoroacetic acid (TFA), sulfonic acid such as methanesulfonic acid, benzenesulfonic acid, p-toluenesulfonic acid, p-toluenesulfonic acid pyridinium salt, and the like, or mixtures thereof. Preferred acids include TFA, sulfuric acid, methanesulfonic acid, benzenesulfonic acid, p-toluenesulfonic acid, hydrogen chloride and phosphoric acid, more preferably, benzenesulfonic acid and phosphoric acid. After the addition of the acid, the mixture is agitated at a temperature ranging from about 25° C. to about 85° C., preferably from about 45° C. to about 70° C., more preferably from about 60° C. to about 70° C., for a period of about 4-12 hours or until the reaction is complete to provide a salt of the compound of formula (I). The compound of formula (I) is isolated by filtration after cooling to about room temperature and adjusting the pH to a neutral range (for example, about 4.5 to about 7.5, preferably about 6.5 to about 7.5) with a suitable base (for example, sodium hydroxide, potassium hydroxide, sodium carbonate, potassium carbonate, sodium hydrogen carbonate, potassium hydrogen carbonate, potassium hydrogen phosphate, potassium phosphate, and the like).

Suitable solvents include, but are not limited to, acetonitrile, tetrahydrofuran, dioxane, N-methylpyrrolidone, N,N-dimethylformamide, dimethylsulfoxide, toluene, methyl tert-butyl ether, dimethoxyethane, alcohols (for example, methanol, n-propanol, isopropanol, and ethanol or mixtures thereof), water, or a mixture of one of the aforementioned solvents with water. The solvent used is most preferably water.

The compound of formula (I) in a suitable solvent is then treated with an acid to provide an acid addition salt of compound of formula (I). Non-limiting examples of acids that can be used include citric acid, malic acid, L-malic acid, D-malic acid, maleic acid, tartaric acid, D-tartaric acid, L-tararic acid, oxalic acid, S-mandelic acid, succinic acid, acetic acid, trifluoroacetic acid, and the like, or mixtures thereof. Preferred acids include maleic acid, D-tartaric acid, L-tartaric acid, succinic acid, oxalic acid, S-mandelic acid, and L-malic acid, preferably L-malic acid. The L-malate salt of the compound of formula (I) is crystalline and is useful in large-scale synthesis for ease of purification and isolation. The reaction is conducted by mixing an aqueous solution of the compound of formula (I) with an $C_{1-6}$ alcoholic solution (preferably $C_{1-4}$ alcohols such as methanol, ethanol, n-propanol, isopropanol and butanol, more preferably methanol, ethanol, and isopropanol) of a suitable acid and the mixture is preferably heated to a temperature ranging from about 30° C. to about 80° C., preferably from about 50° C. to about 70° C., more preferably from about 65° C. to about 70° C., for a period of about 1 hour to about 2 hours, or until the solid dissolves. The mixture is concentrated to remove water and the solid is isolated by filtration.

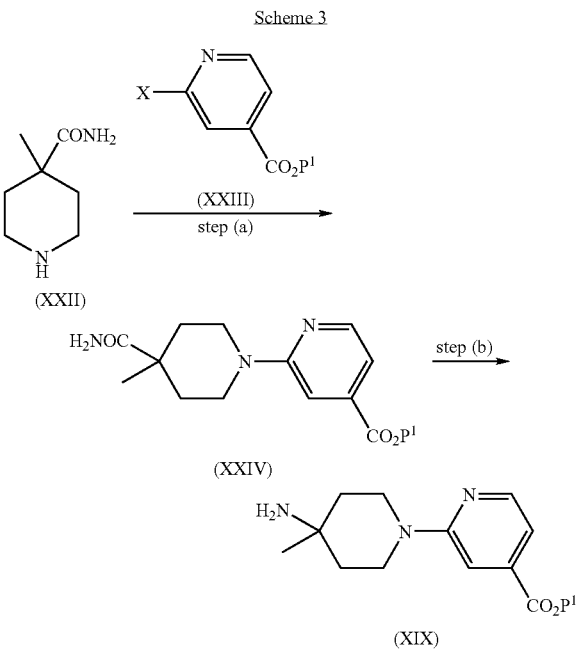

Scheme 3

Scheme 3 illustrates the preparation of a compound of formula (XIX) or salts thereof, wherein P¹ is an acid protecting group.

In step (a), a compound of formula (XXIII) wherein X is Cl, Br, F, I, methanesulfonate or p-toluenesulfonate, and P¹ is an acid protecting group, is treated with a compound of formula (XXII) or salts thereof, in a suitable solvent, to produce a compound of formula (XXIV). A preferred embodiment is directed to the reaction of compound of formula (XXIII) wherein X is Cl and P¹ is $C_{1-6}$ alkyl with a compound of formula (XXII) or salts thereof, to provide a compound of formula (XXIV). More preferably, P¹ is tert-butyl.

A suitable base is optionally used in the reaction to pick up the formation of the acid as the reaction proceeds, and hence facilitates the reaction. In the instances where a salt of the compound of formula (XXII) is used, the presence of a base can also be advantageous to the reaction by converting the salt to a free base in situ, hence improving the availability of the nitrogen to the other reactant.

Hence a mixture of compound of formula (XXIII), a base (about 1 to about 5 molar equivalent with respect to the amount of (XXIII), preferably, about 2 to about 4 molar equivalents, ad more preferably, about 3.5 to about 4 molar equivalents), and about 1.5 equivalents of compound of formula (XXII) relative to compound (XXIII), or salt of compound of formula (XXII), in a suitable solvent are heated to a temperature from about 50° C. to about 150° C., preferably from about 80° C. to about 120° C., and more preferably from about 95° C. to about 105° C., to provide a compound of formula (XXIV). Non-limiting examples of base are inorganic bases and organic bases. Inorganic bases include, but are not limited to, metal carbonates (for, example, sodium carbonate, potassium carbonate, cesium carbonate, lithium carbonate, and the like), metal hydrogen carbonates (for example sodium or potassium hydrogen carbonate), metal phosphates (erg, sodium phosphate, potassium phosphate, and the like), metal tert-butoxides (e.g. sodium and potassium tert-butoxides) and metal hydrogen phosphates (e.g. sodium hydrogen phosphate, potassium hydrogen phosphate, and the like). Organic bases include, but are not limited to, tertiary amines (for example, N-methylmorpholine, DBU, trialkylamines with branched or unbranched $C_{1-6}$ alkyl groups, e.g. diisopropylethyl amine, triethylamine and the lice), pyridine, picolines and the like. Preferred bases are metal carbonates, metal hydrogen carbonates, metal phosphates, metal tert-butoxides, metal hydrogen phosphates, trialkylamines, pyridine and N-methylmorpholine, preferably metal carbonates such as potassium carbonate, Non-limiting examples of suitable solvents include aromatic solvents such as, e.g. benzene, toluene, xylenes and the like, ethers (erg, tetrahydrofuran, diethylether, tert-butylmethyl ether, dimethoxyethane, dioxane, and the like), lactams (for example, 1-methyl-2-pyrrolidinone), N,N-dimethylamides of formic acid or aliphatic $C_{1-6}$ carboxylic acids (for example, N,N-dimethylformamide, N,N-dimethylacetamide and the like), sulfoxides (e.g. dimethylsulfoxide), aliphatic ketones such as, e.g. acetone, methyl ethyl ketone, methyl isobutyl ketone, and the like, and mixtures thereof. Preferred solvents are ethers (preferably dioxane), aromatic solvents (preferably toluene) dimethylsulfoxides, lactams (for example, 1-methyl-2-pyrrolidinone), ethers or mixtures thereof, preferably toluene, dioxane, tetrahydrofuran, dimethylsulfoxide, N-methylpyrrolidone and mixture of dimethylsulfoxide and toluene.

In step (b), a mixture of compound of formula (XXIV) wherein $P^1$ is an acid protecting group, (preferably, $C_{1-6}$ alkyl, more preferably tert-butyl) and at least an equimolar amount of a base in a suitable solvent is maintained at a temperature ranging from $-10°$ C. to about $10°$ C., preferably from about $-5°$ C. to about $5°$ C., more preferably from $-5°$ C. to about $0°$ C., followed by the addition of a suitable halogenating reagent. The mixture is agitated at a temperature ranging from $-10°$ C. to about $10°$ C., preferably from about $-5°$ C. to about $5°$ C., more preferably from $-5°$ C. to about $0°$ C., for a period of about 5 minutes to about 60 minutes, or until the reaction is complete, to yield a compound of formula (XIX). Suitable bases that can be used in step (b) include, but are not limited to, metal hydroxides (e.g. sodium or potassium hydroxide), and metal carbonates (egg sodium or potassium carbonates). Preferred bases are metal hydroxides. The base can be added in solid form or as an aqueous solution, Non-limiting examples of suitable solvents that can be used include polar aprotic solvents such as ethers (e.g. tetrahydrofuran, dioxane, diethyl ether, tert-butylmethyl ether, dimethoxyethane, and the like), acetonitrile, aliphatic ketones (egg acetone, methyl ethyl ketone, methyl isobutyl ketone, and the like), and mixtures thereof. Particularly preferred are acetonitrile and ether solvents such as tetrahydrofuran, dioxane, diethyl ether, tert-butylmethyl ether, dimethoxyethane, and the like. More preferred is ether solvent, preferably tetrahydrofuran Water can optionally be added to all the solvents before the addition of the base, or be introduced as the aqueous solution of the base. Depending on the miscibility of the organic solvents and water, a phase transfer catalyst can be employed in step (b). Non-limiting examples of phase transfer catalysts include tetrabutyl ammonium halides (i.e. tetrabutyl ammonium iodide, tetrabutyl ammonium bromide, tetrabutyl ammonium fluoride and tetrabutyl ammonium chloride), methyl tricapryl ammonium chloride, triethyl benzyl ammonium chloride, tetrabutyl ammonium hydrogen sulfate, methyl tributyl ammonium chloride, tetraphenyl phosphonium bromide, tetrabutyl phosphonium bromide, PEG-500 dimethyl ether; butyl diglyme, and dibenzo-18-crown-6. Preferred phase transfer catalyst is tetrabutyl ammonium bromide, Non-limiting examples of halogenating reagents include N-chlorosuccinimide, bleach, 1,3-dichloro-5,5-dimethylhydantoin, bromine, sodium hypobromite and 1,3-dibromo-5,5-dimethylhydantoin, preferably 1,3-dibromo-5,5-dimethylhydantoin.

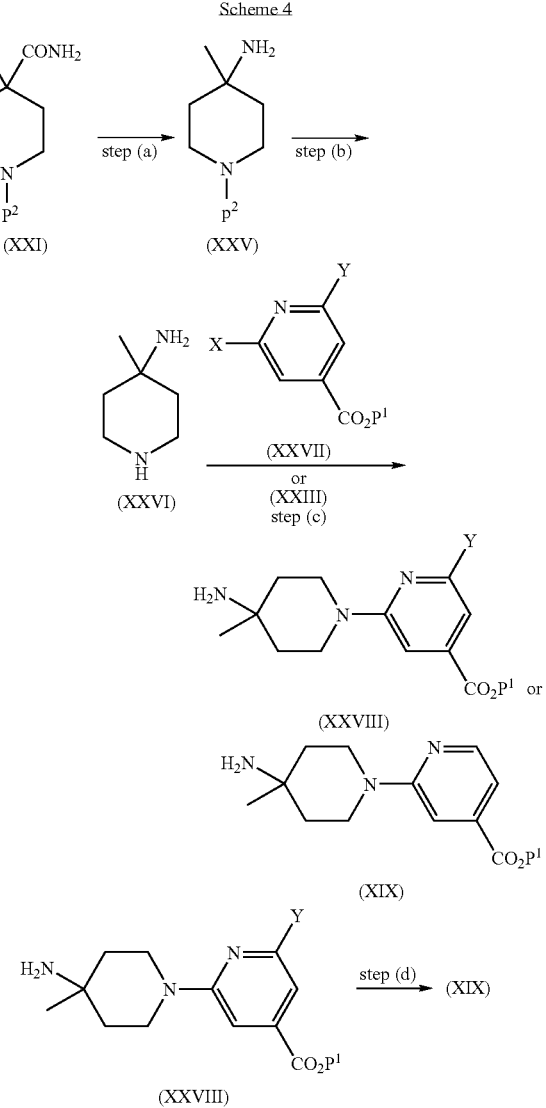

Scheme 4 illustrates an alternative preparation of the compound of formula (XIX) or salts thereof.

In step (a) a compound of formula (XXI) wherein $P^2$ is an amine protecting group is treated with a halogenating reagent and a base in a suitable solvent using the reaction conditions as described in step (b) of Scheme 3. Suitable examples of bases, halogenating reagents and solvents for the reaction are as described in the preceding paragraph. Preferred base is sodium hydroxide or potassium hydroxide and can be used in solid form or as an aqueous solutions. When added as solid, water is introduced separately into the reaction vessel, preferably pre-mixed with the solvent of choice. Preferred solvent is one that is miscible with water, for example, acetonitrile or tetrahydrofuran, particularly, acetonitrile. Preferred halogenating reagent is 1,3-dibromo-5,5-dimethylhydantoin. The reaction mixture is agitated at a temperature ranging from about −10° C. to about 10° C., preferably at about −5° C. to about 5° C.

In step (b), the compound of formula (XXV) or salts thereof, wherein $P^2$ is an amine-protecting group, is deprotected to yield a compound of formula (XXVI) or salts thereof. Preferably, a compound of formula (XXV) wherein $P^2$ is $C_{1-6}$ alkoxy carbonyl, particularly, tert-butoxy carbonyl, in a solvent, is treated with an acid at a temperature ranging from about 25° C. to about 100° C., preferably from about 40° C. to about 80° C., more preferably from about 60° C. to about 70° C., for a period of about 1 hour or until the reaction is complete, to produce compound of formula (XXVI) or salts thereof. Non-limiting examples of acids that can be used include hydrogen chloride (gaseous or in a solvent such as, but not limited to, water, dioxane, methanol), sulfuric acid, phosphoric acid, trifluoroacetic acid (TFA), alkylsulfonic acid such as methanesulfonic acid, benzenesulfonic acid, p-toluenesulfonic acid, and the like, or mixtures thereof. Preferred acids are p-toluenesulfonic acid, trifluoroacetic acid, hydrogen chloride, methanesulfonic acid, and benzenesulfonic, preferably p-toluenesulfonic acid. Non-limiting examples of solvents that can be used in step (a) are protic solvents such as $C_{1-6}$ alcohols, water and mixtures thereof. Preferably, water or branched or unbranched $C_{1-4}$ alcohols (e.g. methanol, n-propanol, isopropanol, ethanol, butanol and mixtures thereof) are used as the protic solvents. The solvent used is most preferably methanol, ethanol, isopropanol, and mixture thereof. Compounds of formula (XXVI) can be isolated as a salt or if desired, can be converted to neutral species during work up, or after isolation by treatment with an appropriate base (for example, metal hydroxides, metal carbonates or metal hydrogen carbonates), rising techniques that are known to one skilled in the art.

In step (c), a compound of formula (XXVII) or (XXIII) wherein X is F, I, Cl, Br, methanesulfonate or p-toluenesulfonate, Y is F, I, Cl or Br, and $P^1$ is an acid protecting group (preferably $C_{1-6}$ alkyl, more preferably tert-butyl), is treated with the compound of formula (XXVI) or salts thereof, in a solvent, using reaction conditions as described in step (a) of Scheme 3, to provide compounds of formula (XXVIII) or (XIX) respectively, Non-limiting and preferred examples of bases and solvents that can be used in step (c) are as described in step (a) of Scheme 3.

Step (d) includes de-halogenating the compound of formula (XXVIII) wherein Y is Cl, Br, I or F and $P^1$ is an acid protecting group (preferably $C_{1-6}$ alkyl and more preferably tert-butyl) to yield a compound of formula (XIX). This can be accomplished by reacting the compound of formula (XXVIII) with hydrogen, with or without a base, and a catalyst, in a solvent. The presence of a base is advantageous to the reaction by soaking up the acid produced during the course of the reaction. Accordingly, one embodiment of the invention is directed to the reaction of the compound of formula (XXVIII) with hydrogen, a base and a catalyst, in a solvent to provide a compound of formula (XIX). The mixture is agitated at a temperature ranging from about 25° C. to about 75° C., preferably at about 40° C. to about 50° C., for a period of about 4 hours or until the reaction is complete. Suitable catalysts for this step include, but are not limited to, palladium/aluminum oxide and palladium on Carbon. Suitable examples of bases include, but are not limited to, metal phosphates (e.g. potassium phosphate, sodium phosphate, and the like), metal hydrogen phosphates (e.g. sodium and potassium hydrogen phosphates), trialkylamines (e.g. triethylamine, diisopropylethylamine, and the like), metal hydroxides (e.g. sodium hydroxide, potassium hydroxide, lithium hydroxide, and the like), metal carbonates (for example, potassium or sodium carbonate) and metal hydrogen carbonates (for example potassium or sodium hydrogen carbonate). Preferred bases are metal phosphates. Suitable examples of solvents are tetrahydrofuran, dioxane, and N-methylpyrrolidone, preferably N-methylpyrrolidone. Preferably, step (d) is conducted in the presence of hydrogen, palladium/aluminum oxide and potassium phosphate in N-methylpyrrolidone.

Scheme 5

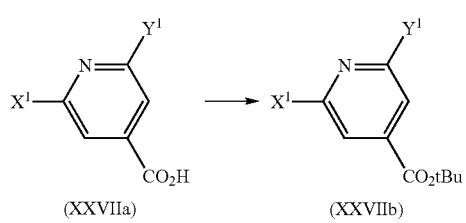

(XXVIIa)    (XXVIIb)

Scheme 5 illustrates the synthesis of a compound of formula (XXVIIb) from (XXVIIa) wherein $X^1$ is F, Cl, Br, I, methanesulfonate or p-toluenesulfonate, and $Y^1$ is H, F, Cl, Br or I.

The transformation is achieved by treating a compound of formula (XXVIIa) with di-tert-butyl dicarbonate in the presence of 4-dimethylaminopyridine (DMAP), with or without a base, in a solvent, at a temperature ranging from about 20° C. to about 35° C., preferably at about room temperature, for a period of about 10 hours to about 48 hours, or until the reaction is complete, to provide a compound of formula (XXVIIb). The molar ratio of DMAP to the compound of formula (XXVIIa) is about 0.1 molar equivalent to about 0.4 molar equivalent, preferably, 0.2 molar equivalent to about 0.25 molar equivalent. Suitable examples of bases include, but are not limited to, organic bases such as tertiary amines (for example, N-methylmorpholine, DBU, trialkylamines with branched or unbranched $C_{1-6}$ alkyl groups, e.g. diisopropylethyl amine, triethylamine and the like), and picolines, inorganic bases such as metal hydroxides (e.g. sodium hydroxide, potassium hydroxide, and lithium hydroxide), metal carbonates (e.g. sodium carbonate, cesium carbonate, potassium carbonate), and metal phosphate (e.g. sodium phosphate, potassium phosphate, and the like), preferably trialkylamine. Non-limiting examples of suitable solvents include acetonitrile, aromatic solvents such as, e.g. benzene, toluene, xylenes and the like, ethers (e.g. tetrahydrofuran, diethyl ether, tert-butylmethyl ether, dimethoxyethane, dioxane, and the like), lactams (for example, 1-methyl-2-pyrrolidinone), N,N-dimethylamides of formic acid or aliphatic $C_{1-6}$ carboxylic acids (for example, N,N-dimethylformamide, N,N-dimethylacetamide and the like), sulfoxides (e.g. dimethylsulfoxide), aliphatic ketones such as, e.g. acetone, methyl ethyl ketone, methyl isobutyl ketone, and the like, and mixtures thereof.

Scheme 6

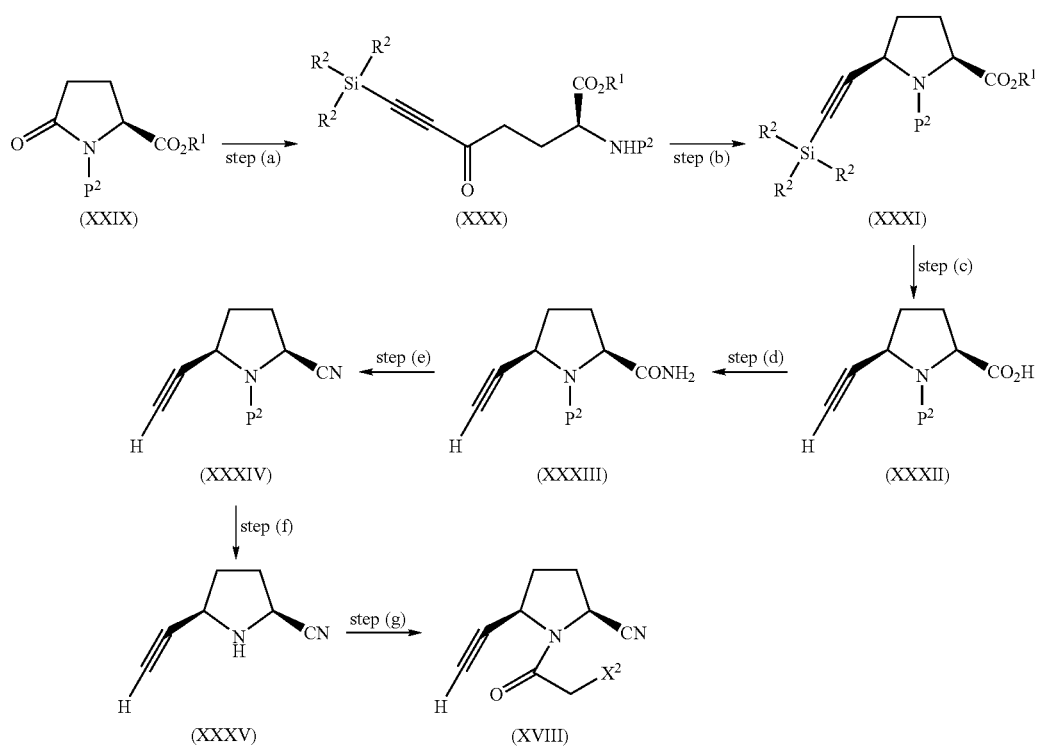

Scheme 6 illustrates the synthesis of the compound of formula (XVIII) wherein $X^2$ is Cl or Br.

In step (a), a compound of formula (XXIX) wherein $R^1$ is an acid protecting group, preferably C1 (alkyl, and more preferably methyl or ethyl, and $P^2$ is an amine protecting group, in a first solvent, is added to a reagent of formula $(R^2)_3Si-CCMgX^3$ wherein $X^3$ is Cl, Br or I and $R^2$ is $C_{1-6}$ alkyl, in a second solvent, at a temperature ranging from about $-20°$ C. to about 25° C., preferably at about $-10°$ C. to about 10° C., and more preferably at about 10° C. to about 0° C. The reaction mixture is agitated for a period of about 1 hour to about 3 hours, or until the reaction is complete, to provide a compound of formula (XXX). The reagent of formula $(R^2)_3Si-CCMgX^3$ used in step (a) is generated in situ by mixing acetylenes of general formula $(R^2)_3SiCC(H)$ with a Grignard reagent of formula $R^3MgX^3$ wherein $R^3$ is $C_{1-10}$ alkyl, phenyl or benzyl, in a second solvent, at a temperature from about $-20°$ C. to about 30° C., preferably at $-15°$ C. to about 15° C., more preferably at $-10°$ C. to about 0° C. Non-limiting examples of the first and second solvents are aprotic polar solvents such as lactams (e.g. 1-methyl-2-pyrrolidinone), N,N-dimethylamides of formic acid or $C_{1-6}$ carboxylic acids (e.g. N,N-dimethylformamide, N,N-dimethylacetamide, and the like), sulfoxides (e.g. dimethylsulfoxide), ethers (e.g. tetrahydrofuran, dioxane, diethyl ether, tert-butylmethyl ether, dimethoxyethane, and the like), and mixtures thereof. Particularly preferred are ether solvents, preferably tetrahydrofuran. First and second solvents can be the same or different, preferably the same. Non-limiting examples of acetylenes of formula $(R^2)_3Si-CCH$ are ethylnyltrimethylsilane, ethynyltriethylsilane and ethynyltriisopropylsilane, preferably ethynyltrimethylsilane. Non limiting, examples of the Grignard reagents used are one of formula $R^3MgX^3$ wherein $R^3$ is ethyl, isopropyl, hexyl, octyl, phenyl, cyclohexyl and benzyl, and $X^3$ is Cl, Br or I, preferably, $R^3$ is ethyl, isopropyl, hexyl or octyl. More preferred are ethynyltrimethyl silane and octylmagnesium chloride in tetrahydrofuran.

Step (b) includes cyclization of the compound of formula (XXX) in the presence of an acid and a reducing agent, in a solvent, at a temperature ranging from about 10° C. to about 40° C., preferably at about 0° C. to about 25° C., more preferably at about 0° C. to about 10° C., to provide a compound of formula (XXXI), Non-limiting examples of reducing agents include sodium triacetoxy borohydride, sodium cyanoborohydride, sodium pivaloyloxy borohydride, triethylsilane and triphenylsilane, preferably sodium triacetoxy borohydride. Suitable acids to be used in step (b) are trifluoroacetic acid, methanesulfonic acid, hydrochloric acid, sulfuric acid and phosphoric acid. Particularly preferred is trifluoroacetic acid. Suitable examples of solvents that can be used are esters of $C_{1-6}$ carboxylic acids, for example, ethyl acetate, isopropyl acetate, n-propyl acetate, n-butyl acetate and the like, or mixtures thereof, preferably isopropyl acetate. More preferably, a mixture of compounds of formula (XXX) and sodium triacetoxy borohydride in isopropyl acetate, at a temperature ranging from about $-10°$ C. to about 40° C., is treated with trifluoroacetic acid and the mixture is agitated at a temperature from about 10° C. to about 25° C., preferably from about 10° C. to about 15° C.

In step (c) the compound of formula (XXXI) in a solvent is saponified, preferably by treatment with a base (added as solid or an aqueous solution) at a temperature from about 0° C. to about 50° C., preferably from about 10° C. to about 30° C., and more preferably from about 20° C. to about 25° C., for about 15 hours or until the reaction is complete, followed by the addition of an acid, to provide the compound of formula (XXXII). Non-limiting examples of suitable bases for step (c) are metal hydroxides (e.g. sodium hydroxide, potassium hydroxide, lithium hydroxide, barium hydroxide and the like) and metal carbonates (e.g. sodium carbonate, potassium carbonate, and cesium carbonate). Particularly preferred bases include metal hydroxides such as sodium hydroxide, potassium hydroxide and lithium hydroxide. Examples of solvents that can be employed are $C_{1-6}$ alcohols, preferably lower alcohols such as methanol, ethanol, isopropanol, n-propanol, n-butanol, and the like, or mixtures thereof. Particularly preferred is ethanol. Water can be optionally added to the alcohols or introduced as an aqueous solution of the base. Treatment of the salt of the compound of formula (XXXII) with an acid provides a compound of formula (XXXII). Suitable acids that can be used include, but are not limited to, hydrochloric acid, phosphoric acid, toluenesulfonic acid, methanesulfonic acid and benzenesulfonic acid, preferably, hydrochloric acid.

Step (d) includes treating the compound of formula (XXXII) with ammonia in the presence of a coupling reagent and a base, in a solvent, to provide a compound of formula (XXXIII). While aqueous ammonia is preferred, it is envisaged that the reaction can otherwise be achieved by use of gaseous or liquid ammonia, or a solution of ammonia in tetrahydrofuran, toluene, dioxane or in $C_{1-6}$ alcoholic solvents such as isopropanol. Examples of coupling reagents suitable for step (d) include, but are not limited to, chloroformates, thionyl chloride, oxalyl chloride and other commonly used coupling reagents for amide bond formation known to one skilled in the art, e.g. EDCI/HOBT. Particularly preferred are phenyl chloroformate and chloroformates of formula ClCOO($C_{1-6}$ alkyl) such as, for example, isobutyl chloroformate and ethylchloroformate. Isobutyl chloroformate is particularly preferred. The reaction is facilitated by the use of a suitable base. Suitable bases include ammonia, organic bases such as pyridine, picoline and tertiary amines (includes tri($C_{1-6}$ alkyl) amines such as diisopropylethyl amine, triethylamine and the like, and cyclic tertiary amines such as N-methylmorpholine, DBU and the like), and inorganic bases such as metal hydrogen carbonates (e.g. sodium or potassium hydrogen carbonates), metal phosphates (e.g. sodium or potassium phosphate) and metal carbonates (e.g. sodium, potassium or cesium carbonate). Particularly preferred are metal hydrogen carbonates, metal phosphates, metal carbonates and organic bases, preferably, sodium hydrogen carbonate, potassium hydrogen carbonates pyridine, aliphatic tertiary amines such as tri($C_{1-6}$ alkyl)amines (e.g. triethylamine, diisopropylethylamine, and the like) and cyclic tertiary amines (e.g. N-methylmorpholine, DBU, and the like). Non limiting examples of solvent that can be used for the process include aprotic polar solvents such as ketones, ethers, esters of $C_{1-6}$ carboxylic acids, lactams, and sulfoxides, preferably esters and ether solvents, for example ethyl acetate, isopropyl acetate, tetrahydrofuran and the like. The reaction is conducted by treating the compound of formula (XXXII) in a solvent (preferably isopropyl acetate, tetrahydrofuran, diethyl ether, dioxane, or methyl tert-butyl ether) with about 1 to about 2 molar equivalents of a chloroformate (e.g. isobutyl chloroformate), preferably about 1.1 to about 1.3 molar equivalents, in the presence of about 1.2 to about 1.4 molar equivalents of a tertiary amine (preferably N-methylmorpholine, triethylamine, diisopropylethylamine or mixtures thereof) at a temperature ranging from about −20° C. to about 50° C., preferably at about −10° C. to about 10° C. for a period of about 30 minutes to about 90 minutes or until the formation of the intermediate is complete. The reaction mixture is then treated with ammonia (preferably aqueous ammonia or ammonia gas) at a temperature ranging from about −10° C. to about 30° C., preferably from about 0° C. to about 25° C., more preferably at about 0° C. to about 15° C., for about 30 minutes to about 3 hours or until the reaction is complete.

Step (e) includes dehydrating the compound of formula (XXXIII) to provide a compound of formula (XXXIV). One can accomplish this with a dehydrating agent such as phosphorous pentoxide, phosphoryl chloride/pyridine or thionyl chloride/DMF, preferably thionyl chloride/DMF, in a solvent, at a temperature ranging from about −10° C. to about 25° C., preferably at about 0° C. to about 15° C., to generate a compound of formula (XXXIV). Suitable solvents are polar aprotic solvents, preferably pyridine, ether solvents (tetrahydrofuran, 2-methyltetrahydrofuran, dioxane, methyl tert-butyl ether and the like), ester, solvents, or mixtures thereof. Particularly preferred are tetrahydrofuran, 2-methyltetrahydrofuran, dioxane, methyl tert-butyl ether, isopropyl acetate, pyridine, or mixtures thereof.

In step (f), the compound of formula (XXXIV) wherein $P^2$ is an amine-protecting group (preferably $C_{1-6}$ alkoxy carbonyl, more preferably tert-butoxycarboxyl) is deprotected to produce a compound of formula (XXXV) or salts thereof. This can be achieved by treatment with an acid, in a solvent, at a temperature ranging from about 10° C. to about 50° C., preferably at about 20° C. to about 25° C. Non-limiting examples of acids that can be include hydrogen chloride (gaseous or in a solvent such as, but not limited to, water; dioxane, methanol), sulfuric acid, nitric acid, phosphoric acid, trifluoroacetic acid (TFA), methanesulfonic acid, p-toluenesulfonic acid and benzenesulfonic acid. Preferred acids are p-toluenesulfonic acid, trifluoroacetic acid, hydrogen chloride, methanesulfonic acid, and phosphoric acid. Suitable solvents for this step include protic polar solvents and polar aprotic solvents, preferably acetonitrile, ethers such as tetrahydrofuran, $C_{1-6}$ alcohols such as isopropanol, methanol, and ethanol, or mixtures thereof. Basifying the reaction mixture in situ after completion of the reaction with about 1 molar equivalent of an appropriate base (for example, trialkylamines, metal carbonates, metal hydroxides, metal phosphates and metal hydrogen carbonates, wherein the metal portion of metal carbonates, metal hydroxides, metal phosphates) at a temperature of about 0° C. to about 25° C., preferably at about 10° C. to about 20° C., affords the compound of formula (XXXV). The compound of formula (XXXV) or salts thereof can or cannot be isolated.

Step (g) involves treatment of the compound of formula (XXXV) or salts thereof from step (f) with a reagent of the formula $X^2CH_2COY^2$ wherein $X^2$ and $Y^2$ are independently Cl or Br, preferably $X^2$ and $Y^2$ are Cl, and a base, in a solvent, at a temperature from about −10° C. to about 25° C., preferably at about 0° C. to about 10° C., to produce a compound of formula (XVIII). Suitable bases for step (g) include organic bases such as pyridine, or tertiary amines such as trialkylamine (e.g. triethylamine, diisopropylethylamine, and the like) and cyclic tertiary amines (egg N-methylmorpholine, DBU, and the like), metal hydrogen carbonates (e.g. sodium or potassium hydrogen carbonates), metal carbonates (e.g. sodium, potassium, or cesium carbonates), metal hydroxides (e.g. sodium, potassium and lithium hydroxides), metal phosphates (e.g. sodium or potassium phosphates) or metal hydrogen phosphates (e.g. sodium or potassium hydrogen phosphates), preferably metal hydroxides (e.g. lithium hydroxide, sodium hydroxide or potassium hydroxide) and trialkylamines such as diisopropylethyl amine and triethylamine. Suitable solvents include, for example, polar aprotic solvents such as ether solvents (e.g. tetrahydrofuran, diethyl ether, tert-butyl methyl ether), ketones (erg acetone), acetonitrile, esters of $C_{1-6}$ carboxylic acids, lactams, sulfoxides, and N,N-dimethylamides of formic acid or $C_{1-6}$ carboxylic acids, or mixtures thereof. Water is optionally added to an organic solvent such as tetrahydrofuran, tert-butyl methyl ether and toluene. Preferred solvents are ethers solvents and acetonitrile. About 1 to about 1.5 molar equivalents of the base with respect to the compound of formula (XXXV) is used. In the instance that the salt of the compound of formula (XXXV) is employed, about 2 to about 2.5 molar equivalents of the base is added.

ally, the reaction can be performed in the presence of a co-solvent. Non-limiting examples of suitable co-solvents include aromatic hydrocarbons such as toluene, benzene, and xylene, halogenated hydrocarbons such as chloroform, carbon tetrachloride and dichloromethane, or mixtures thereof. The catalyst used in the asymmetric hydrogenation is commercially available [(1S,2S)—N-(p-toluensulfonyl)-1,2-diphenylethanediamine](p-cymene) ruthenium (I) (CAS

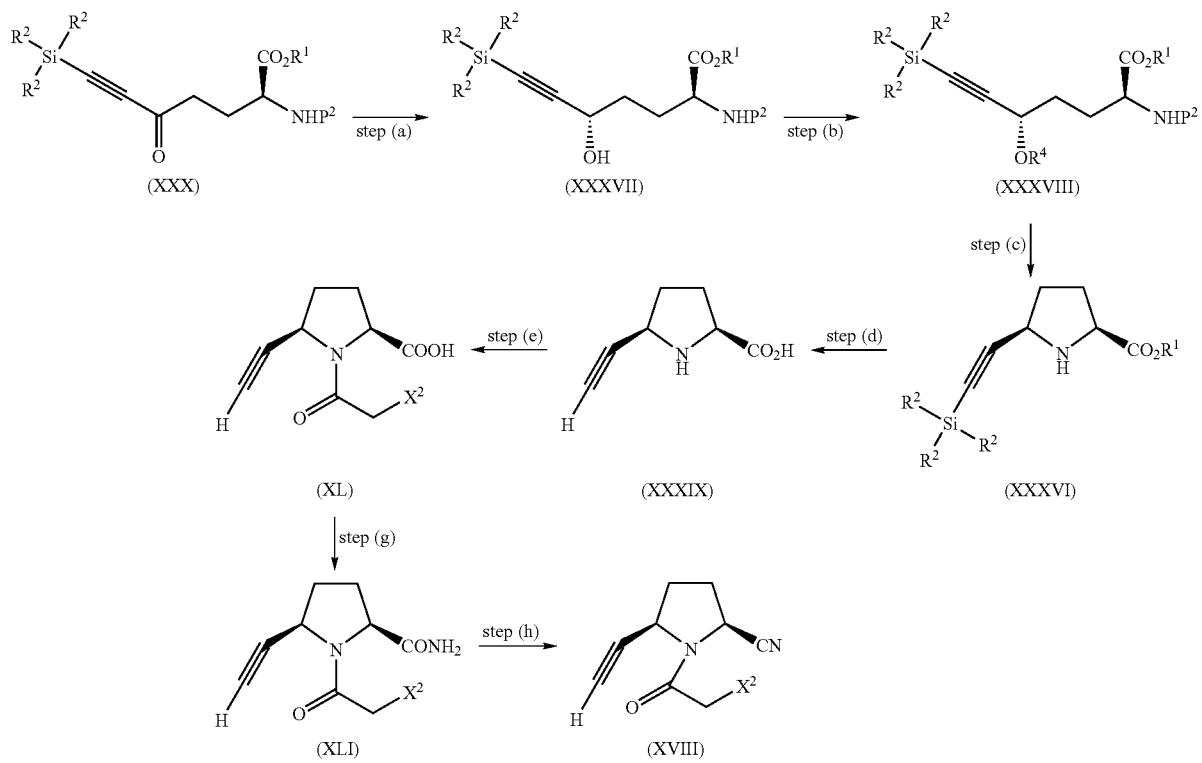

Scheme 7 outlines another synthetic route for the preparation of the compound of formula (XVIII).

In step (a) the compound of formula (XXX) wherein $R^1$ is an acid protecting group (preferably $C_{1-6}$ alkyl such as for example, methyl, ethyl, isopropyl tert-butyl and the like), $R^2$ is $C_{1-6}$ alkyl (for example, methyl, ethyl, isopropyl, and the like), and $P^2$ is an amine protecting group (preferably alkoxycarbonyl such as, for example, tert-butoxycarbonyl and the like), is subjected to asymmetric reduction to provide a compound of formula (XXXVII). Asymmetric reduction can be accomplished by either asymmetric hydrogenation in the presence of a catalyst or chiral hydride transfer. The hydrogenation is generally carried out in oxygen-free conditions, conveniently under inert gas (e.g. argon) or a hydrogen atmosphere. However, it is not essential for the reaction that the hydrogen for, the hydrogenation be derived from the atmospheric gas through the reaction mixture. The hydrogen can also be produced in situ in solution from suitable hydrogen sources. Hydrogen sources of this kind include e.g. ammonium formate, formic acid and other formates, hydrazines in the presence of metal ions such as $Fe^{2+}/Fe^{3+}$, and secondary $C_{1-6}$ alcohols such as isopropanol, 2-butanol and 3-pentanol, preferably secondary $C_{1-6}$ alcohols and more particularly, isopropanol. The secondary alcohol used for the hydrogen source is also the solvent system used for the reaction Option-

188444-42-0. Kanto Chemical Co. Inc., catalog #41067-65). This catalyst can also be prepared as described in Angew. Chem. Int. Ed. Engl., 1997, 36, No. 3, p, 287. About 0.001 to about 0.02 molar equivalent of the catalyst relative to (XXX) is used, preferably, about 0.001 to about 0.01, and more particularly, 0.001 to about 0.005. The reaction time is generally between 2 and 12 hours up to its completion, preferably between 2 and 4 hours. A process is preferred wherein the asymmetric hydrogenation is conducted in a temperature range of about 20° C. to about 40° C., particularly about 20° C. to about 25° C.

Step (a) can also be accomplished by chiral hydride transfer. Chiral hydride transfer can be carried out by treatment of a compound of formula (XXX) with a chiral reducing agent or reducing agent/chiral ligand in a solvent. Non-limiting examples of solvents include ether solvents (preferably tetrahydrofuran) or non-polar solvents such as toluene, benzene, xylene (preferably toluene). Examples of chiral reducing agents are, but not limited to, (R)-Alpine borane (9-Borabicyclo[3.3.1]nonane, 9-(2,6,6-trimethylbicyclo[3.1.1]hept-3-yl)-, [1R-(1α,2β,3α,5α)]). Examples of reducing agents/chiral ligands include catacholborane/1-butyl-3,3-diphenylhexahydropyrrolo[1,2-c][1,3,2]oxazaborole, lithium aluminum hydride/(2R,3R)-4-dimethylamino-3-methyl-1,2-diphenyl-butan-2-ol, and BINAL-H (lithium aluminum hydride in the presence of 1,1'binaphthalene-2,2'-diol and ethanol).

Step (b) encompasses activation of the hydroxy moiety of the compound of formula (XXXVII) by treatment with an activating reagent Non-limiting examples of activating agent include trihaloacetic anhydride (such as trifluoroacetic anhydride, tribromoacetic anhydride or trichloroacetic anhydride) and a reagent of formula $R^4X$ wherein $R^4$ is trihaloacetyl (e.g. trifluoroacetyl, tribromoacetyl or trichloroacetyl), methanesulfonyl, benzenesulfonyl, p-toluenesulfonyl and X is Cl, Br or I. The reaction is generally carried out in the presence of a base selected from, but not limited to, an organic base and inorganic base. Suitable organic bases are tertiary amines such as tri($C_{1-6}$ alkyl) amines (e.g. triethylamine, diisopropylethyl amine, trimethylamine and the like), and tertiary cyclic amines (for example, N-methyl morpholine, DBU, 1,5-diazabicyclo-[4.3.0]non-5-ene, 1,8-diazabicyclo-[5.4.0]undec-7-ene, and the like), pyridine, and picolines. Suitable inorganic bases are metal salts such as metal carbonates (e.g. carbonates of sodium, potassium, barium and cesium), metal hydrogen carbonates (e.g. hydrogen carbonates of sodium and potassium) and metal phosphates (e.g. phosphates of sodium and potassium). The present invention provides a process for making a compound of formula (XXXVIII) without isolation including the step of reacting the compound of formula (XXXVII), an activating reagent and a base, in a solvent, at a temperature from about −10° C. to about 50° C., preferably about −10° C. to about 10° C., for a period of about 10 minutes to about 2 hours, or until completion of the reaction. Suitable solvents that can be used include for example chlorinated hydrocarbon such as chloroform or dichloromethane, ethers (e.g. tetrahydrofuran, diethyl ether, methyl tert-butyl ether, and the like) and esters of $C_{1-6}$ carboxylic acid (e.g. isopropyl acetate, ethyl acetate and the like). The intermediate compound of formula (XXXVIII) is not isolated and is then subjected to reaction conditions of step (c) to provide a compound of formula (XXXVI).

In step (c), the intermediate (XXXVIII) wherein $P^2$ is an amine protecting group (preferably, alkoxycarbonyl and more particularly tert-butoxy carbonyl) is deprotected by treatment with an acid at a temperature from about 0° C. to about 50° C., preferably about 20° C. to about 30° C., and more preferably at about room temperature, for a period of about 30 minutes to about 4 hours, typically for about 2 hours, or until the reaction is complete. Upon treatment with base, the intermediate amine formed cyclizes to provide the compound of formula (XXXVI). Suitable acids that can be used in the deprotection include, but are not limited to, hydrogen chloride (gaseous or in a solvent such as, but not limited to, dioxane, water, acetic acid or methanol), sulfuric acid, phosphoric acid, trifluoroacetic acid (TFA), sulfonic acid such as methanesulfonic acid, benzenesulfonic acid, p-toluenesulfonic acid, and the like, or mixtures thereof, preferably hydrogen chloride, TFA, sulfuric acid, p-toluenesulfonic acid and phosphoric acid. The acid salt of the intermediate formed by deprotection of (XXXVIII) is re-dissolved in a suitable solvent after concentration and is treated with a base. The reaction mixture is stirred for a period of about 10 minutes to about 2 hours, or until the reaction is complete, typically for about 30 minutes, at a temperature from about 0° C. to about 35° C., typically at about room temperature, to provide a compound of formula (XXXVI). Suitable bases include, but are not limited to, metal carbonates (e.g. potassium, sodium or barium carbonates), metal hydrogen carbonates (e.g. potassium or sodium hydrogen carbonates) and metal phosphates (egg sodium or potassium phosphates). Suitable solvents include ethers (for example tetrahydrofuran), acetonitrile, N,N-dimethylformamide, N,N-dimethylacetamide and dimethylsulfoxide.

In step (d), the compound of formula (XXXVI) or salts thereof is saponified by treatment with a suitable inorganic base to provide a compound of formula (XXXIX). Thus, the compound of formula (XXXVI) in a suitable solvent at a temperature of about −10° C. to about 30° C., preferably at about 0° C. to about 30° C., is added a suitable inorganic base (added as solid or an aqueous solution) and the mixture stirred for about 10 minutes to about 2 hours, or until the reaction is complete. The base employed is about 0.9 to about 1.5 equivalents, preferably about 1.0 to about 1.2 equivalents, relative to the compound (XXXVI). In the event that a salt of (XXXVI) is used in the reaction, the quantity of the base used relative to (XXXVI) is about 1.9 to about 2.5 equivalents, preferably about 2.0 to about 2.2 equivalents. Non-limiting examples of suitable bases for step (d) are metal hydroxides (e.g. sodium hydroxide, potassium hydroxide, lithium hydroxide, barium hydroxide and the like) and metal carbonates (e.g. sodium carbonate, potassium carbonate, and cesium carbonate). Particularly preferred bases include metal hydroxides such as sodium hydroxide, potassium hydroxide and lithium hydroxide. Examples of solvents that can be employed are ethers (erg, tetrahydrofuran, diethyl ether, methyl tert-butyl ether, and the like), or $C_{1-6}$ alcohols, preferably lower alcohols such as methanol, ethanol, isopropanol, n-propanol, n-butanol, and the like, or mixtures thereof. Water can be optionally added to the alcohols or introduced as an aqueous solution of the base, Particularly preferred solvent is tetrahydrofuran.

The compound of formula (XXXIX) or salts thereof, in a suitable solvent, is cooled to a temperature range of about −10° C. to about 10° C., preferably at about −5° C. to about 5° C., and about one equivalent of a reagent of formula $X^2CH_2COY^2$ wherein $X^2$ and $Y^2$ are independently Cl or Br is added, in the presence of a base, and the mixture is agitated at about −10° C. to about 10° C., preferably at about −5° C. to about 5° C., for about 30 minutes to about 3 hours, or until the reaction is complete, to provide a compound of formula (XL). Suitable base and solvent for the conversion are as set fourth in step (g) of Scheme 6.

Compound of formula (XL) is converted to compounds of formula (XLI) and (XVIII) respectively using reaction conditions described in steps (d) and (e) of Scheme 6.

The present invention will now be described in connection with certain preferred embodiments, which are not intended to limit its scope. On the contrary, the present invention covers all alternatives, modifications, and equivalents as can be included within the scope of the claims, Routine experimentation, including appropriate manipulation of the reaction conditions, reagents used and sequence of the synthetic route, protection of any chemical functionality that can not be compatible with the reaction conditions, and deprotection at suitable point in the reaction sequence of the method are included in the scope of the invention

EXAMPLES

Example 1

Methyl (2S)-2-[(tert-butoxycarbonyl)amino]-5-oxo-7-(trimethylsilyl)hept-6-ynoate A 2-L, 3-neck jacketed round bottomed flask equipped with an overhead mechanical stirrer, $N_2$-inlet and temperature probe was charged with octylmagnesium chloride (2.1 M, 248.3 g, 0.560 mol) and tetrahydrofuran (1 vol, 102 g) and the solution was chilled to 0° C. (internal temperature). Trimethylsilyl acetylene (57.5 g, 0.585 mol) was added subsurface by syringe over about 25 min ($T_{max}$=13° C.). The solution was stirred at 0° C. for 1 hour and was then cooled to −10° C. (internal temperature). A solution of (S)-1-tert-butyl 2-methyl 5-oxopyrrolidine-1,2-dicarboxylate (125 g, 0.509 mmol) in tetrahydrofuran (250 g) was added subsurface by rotary pump over a 2-hour period. The flask and pump were rinsed with about 25 g of tetrahydrofuran, which was added to the reaction flask. The reaction was monitored by HPLC until completion. A 2-L flask was charged with water (870 g) and $NH_4Cl$ (174 g) and the contents were mixed until all of the solid dissolved. About ½ of the 20% $NH_4Cl$ solution (504 g) was removed Isopropyl acetate (380 g) was added to the flask and the mixture was cooled to <5° C. The reaction solution was added to the isopropyl acetate/$NH_4Cl$ solution over about 20 minutes ($T_{max}$=5° C.). The bath was removed and the mixture was allowed to warm to above 10° C. The mixture was transferred to a separatory funnel and the layers were separated. The gray semi-solid that was present was kept with the organic layer. The aqueous layer was extracted with isopropyl acetate (328 g) and the organic layers were combined. The organic layer was washed with the remainder of the 20% $NH_4Cl$ solution and with 20% NaCl solution (435 mL). The organic layer was concentrated and diluted with isopropyl acetate a total of two times. The mixture was filtered to remove precipitated salts. The isopropyl acetate solution of the title compound was used directly in the next step.

Example 2

(5R)-1-(tert-butoxycarbonyl)-5-prop-1-ynyl-L-proline

A 2-L, 3-neck jacketed round-bottomed flask equipped with an overhead mechanical stirrer, $N_2$-inlet, temperature probe and addition funnel was charged with sodium triacetoxyborohydride (93.0 g, 0.44 mol), isopropyl acetate (100 g) and an isopropyl acetate solution obtained from Example 1 (27.8 wt %, 410 g, 0.33 mol). The resulting mixture was chilled to −10° C. (internal temperature). Trifluoroacetic acid (170 g, 1.5 mol) was added dropwise by addition funnel over a 2-hour period. The internal temperature was adjusted to 10° C. and the mixture was stirred until HPLC analysis indicated complete consumption of starting material (about 15 hours). The reaction was poured into 750 g of 25% $K_2HPO_4$ (prepared by dissolving 250 g of $K_2HPO_4$ in 750 g of water). The pH of the mixture was adjusted to 6.6 using 20% KOH (prepared by dissolving 100 g of KOH in 400 g of water). The layers were separated. The organic layer was washed with 25% $K_2HPO_4$ (250 g) and with water (250 g). The organic layer was distilled to remove isopropyl acetate, which was chased with ethanol to a final volume of about 250 mL. The solution was cooled to 0° C. and 3.5 M LiOH solution (prepared by dissolving 37 g of LiOH—$H_2O$ in 250 g of water) was added such that the temperature remained below 20° C. The reaction progress was followed by HPLC until no ester remained (typically about 2 hours). The ethanol was removed by distillation under vacuum and the resulting aqueous layer was extracted with methyl tert-butyl ether (190 g). The methyl tert-butyl ether layer was extracted with water (100 g) and discarded. The combined aqueous layers were cooled to 0° C. and neutralized to pH 7 with concentrated HCl. Isopropyl acetate (220 g) was added and the pH was adjusted to 3 with concentrated HCl. The layers were separated and the aqueous layer was extracted with isopropyl acetate (220 g). The combined organic layers were washed with water (100 g). The organic solution was distilled under vacuum to a total volume of about 180 mL, and cooled to 0° C. Crystals formed over a 30-minute period. Heptanes (50 g) was added dropwise over a 2-hour period and the resulting mixture was stirred for 2 hours at 0° C. The mixture was filtered and the solid was washed with cold 1:1 isopropyl acetate/heptanes (50 mL) and dried under vacuum to afford the title compound. $^1$H NMR (400 MHz, $CDCl_3$) δ ppm 0.24 (s, 9H) 1.45 (s, 9H) 1.87-2.04 (m, 1H) 2.11-2.28 (m, 1H) 2.57-2.81 (m, 2H) 3.75 (s, 3H) 4.23-4.40 (m, 1H) 4.99-5.14 (m, 1H).

Example 3 tert-1-butyl (2S,5R)-2-cyano-5-ethynylpyrrolidine-1-carboxylate

Step A

A 2-L jacketed flask, equipped with an overhead stirrer and a thermocouple was charged with Example 2 product (100.2 g, 6.42 mol), isopropyl acetate (500 mL) and N-methylmorpholine (57 mL, 0.522 mol). Isobutyl chloroformate (65 mL, 0.502 mol) was added dropwise over about 15 minutes and the resulting solution was stirred at 0° C. for 1 hour. A portion of the reaction was quenched into benzyl amine and analyzed by HPLC to evaluate the progress of the mixed anhydride formation. The mixed anhydride formation was typically complete at this stage. The reaction mixture was added to cold (0° C.) 27% $NH_4OH$ solution such that the internal temperature of the quench remained below 25° C. The reaction flask was rinsed with isopropyl acetate (25 mL), which was added to the quench flask. The mixture was diluted with 26% NaCl solution (300 g, prepared by dissolving 80 g of NaCl in 220 g of water) and the layers were separated. The aqueous layer was extracted with isopropyl acetate (100 mL). The combined organic layers were washed with 20% $KH_2PO_4$ (2×500 g) and with brine (200 g). The organic solution was concentrated to a total volume of about 170 mL.

Step B

A clean, 2-L jacketed flask equipped with an overhead stirrer and a thermocouple was charged with tetrahydrofuran (500 mL) and N,N-dimethylformamide (77 mL, 1.0 mol) and the solution was cooled to 0° C. Thionyl chloride (70 mL, 0.961 mol) was added dropwise such that the internal temperature remained below 15° C. The solution was stirred at 0° C. for 1.5 hours. The isopropyl acetate solution of the amide from step A was added such that the internal temperature remained below 25° and the resulting mixture was stirred for 1 hour at 0° C. The reaction solution was added to a cold (0° C.) 5 M NaOH solution such that the internal temperature remained below 25° C. The layers were separated and the organic layer was washed with 20% $KH_2PO_4$ solution (500 g) and 5% NaCl solution (500 g). The organic layer was distilled to a total volume of about 170 mL and was diluted with $CH_3CN$ (500 mL). The organic layer was distilled to a total volume of about 170 mL and was diluted with $CH_3CN$ (500 mL). The organic solution was filtered to remove precipitated salts. The organic layer containing the title compound was used directly in the next step.

Example 4

(2S,5R)-1-(chloroacetyl)-5-ethynylpyrrolidine-2-carbonitrile

A 1-L three-necked round bottom flask equipped with a mechanical stirrer, $N_2$-inlet and temperature probe was charged with the product of the product of Example 3 (40 g, 0.182 mol) as a solution in CH$_3$CN (296.3 g). Additional CH$_3$CN (58.1 g) was added to bring the total to 10 volumes. The temperature of the reaction was adjusted to 25° C. p-Toluenesulfonic acid (70.1 g, 0.363 mol) was added in portions to keep internal temperature below 30° C. CO$_2$ gas evolution was fairly vigorous initially. Venting for CO$_2$ gas was essential. The reaction was stirred overnight at 25° C. during which time the reaction became heterogeneous. Disappearance of the starting material was followed by HPLC and formation of the product was followed by GC. Upon complete deprotection, the reaction was cooled to 0° C. and N,N-diisopropylethylamine (67.8 nm, 399.5 mmol) was added slowly to keep internal temperature below 15° C. The reaction mixture was cooled back to 0° C. and chloroacetyl chloride (24.61 g, 217.9 mmol) was added slowly to keep internal temperature below 15° C. The reaction was mixed at 0° C. and stirred for 1 hour. The reaction mixture was slowly added to a cold solution of isopropyl acetate (400 mL) and 1M K$_2$HPO$_4$ (400 mL). The mixture was concentrated and distilled with isopropyl acetate (800 mL) and water (320 mL) to remove all of the CH$_3$CN. The isopropyl acetate/CH$_3$CN ratio was followed by GC. Upon complete removal of the CH$_3$CN the layers were separated. The aqueous layer was extracted with isopropyl acetate (2×200 mL). The combined organic layers were washed with 1M K$_2$HPO$_4$ (200 mL). The organic layer was dried by repeated distillation from isopropyl acetate and the mixture was filtered to remove precipitated salts. The filtrate was concentrated and diluted with isopropyl alcohol several times. The solution was concentrated to about 90 mL, and stirred until solids began to form. Water (420 mL) was added slowly and the mixture was stirred for about 1 hour at room temperature and for about 1 hour at 0° C. The solid was collected by filtration and washed with cold isopropyl alcohol/water (65 mL) and dried in a vacuum oven for 48 hours at 40° C. to give 27.66 g (77.5% yield) of off-white solid. $^1$H NMR (400 MHz, CDCl$_3$) δ ppm 2.23-2.52 (m, 4H) 2.56 (d, J=1.78 Hz, 1H) 4.31 (dd, J=12.9, 66.8 2H) 4.67-4.94 (in 2H).

Example 5 tert-butyl 2-chloroisonicotinate

A 1-L jacketed 3-neck round bottom flask equipped with overhead stirrer, N$_2$-inlet vented to the atmosphere and thermocouple was charged with 2-chloroisonicotinic acid (78.0 g, 495 mmol), di-tert-t-butyl dicarbonate (230.1 g, 1054 mmol), and 1-methyl-2-pyrrolidinone (179.3 g). A solution of 4-dimethylamino pyridine (11.61 g, 95 mmol) dissolved in 1-methyl-2-pyrrolidinone (60.0 g) was charged to the mixture and the temperature was adjusted to 25±10° C. The reaction was quenched after stirring for about 17 hours by the addition of an ice-cold solution of sodium chloride (30.0 g) and monobasic potassium phosphate (30.2 g) in water (320.7 g). Methyl tert-butyl ether (278 g) was added, and the mixture was stirred and allowed to settle. The layers were separated. The organic phase was washed three times with water (~230-240 g each) then diluted with toluene (239 g) and distilled under vacuum to a red oil (150.8 g, KF 29.9 ppm H$_2$O). $^1$H NMR (400 MHz, CDCl$_3$) δ ppm 1.60 (s, 9H) 7.69-7.72 (m, 1H) 7.79-7.81 (m, 1H) 8.49 (dd, J=5.08, 0.69 Hz, 1H).

Example 6 tert-butyl 2,6-dichloroisonicotinate

To a 12-L flask equipped with an overhead stirrer and a thermocouple was charged 2,6-dichloroisonicotinic acid (875 g, 4.56 mol) and 4-dimethylamino pyridine (110 g, 0.91 mol) followed by 1-methyl-2-pyrrolidinone (2.4 kg). After stirring for 15 minutes to dissolve the solids, di-tert-butyl dicarbonate (2-03 kg, 9.6 mol) was charged as a melt. A water bath (25° C.) was placed around the flask for cooling then triethylamine (450 g, 4.56 mol) was charged over 15 minutes while maintaining the temperature below 35° C. The reaction was complete after 19 hours at about room temperature. The reaction mixture was diluted with methyl tert-butyl ether (6 L) and water (8 L) containing KH$_2$PO$_4$ (840 g, 6.38 mol). After cooling to a temperature<30° C. the aqueous phase was separated and the methyl tert-butyl ether layer was filtered through a Celite® bed to remove insoluble material. The methyl tert-butyl ether layer was then washed with water (2×6 L). To the methyl tert-butyl ether layer was charged Darco-G60 (85 g) and the mixture was stirred for 1 hour and filtered through a Celite® pad. The organic layer was distilled under vacuum to a total volume of, 5 L. The distillation was continued, maintaining the volume by the addition of methanol (8 L). The slurry in methanol was warmed to 50° C. to dissolve the solids and then cooled to ambient temperature to crystallize. Water (1.5 L) was added over 30 minutes. The slurry was filtered and the solid washed with a mixture of methanol (5.0 L) and water (2.0 L) in 2 portions. The cake was dried under vacuum (50° C., nitrogen bleed) resulting in 970 g (88% yield) of light brown powder. $^1$H NMR (400 MHz, CDCl$_3$) δ ppm 1.59 (s, 9H) 7.71 (s, 2H).

Example 7

1-tert-butyl 4-ethyl piperidine-1,4-dicarboxylate

A 1-L round bottom flask equipped with an overhead mechanical stirrer, addition funnel, N$_2$-inlet, vent needle and temperature probe was charged with di-tert-butyl dicarbonate (197.8 g, 0.906 mol) and toluene (170 g) then chilled to 15° C. Ethyl isonipecotate (146.8 g, 0.924 mol) was charged to the addition funnel and then added to the reaction mixture while maintaining the internal temperature not more than 30° C. (addition time 30 min, T$_{max}$=25° C.). The addition funnel was rinsed with toluene (30 g), which was added to the reaction flask. The reaction was mixed for 1 hour and quenched over about 1 minute with a 1M H$_3$PO$_4$ solution (prepared from 180 g water and 20 g H$_3$PO$_4$). The layers were separated. The organic phase was washed with a basic brine solution (prepared from 150 g water, 1.5 g NaOH pellets and 23 g NaCl). The toluene solution was used directly in the next step.

Example 8

1-tert-butyl 4-ethyl 4-methylpiperidine-1,4-dicarboxylate

A 250-mL round bottom flask equipped with an overhead mechanical stirrer, addition funnel, N$_2$-inlet and temperature probe was charged with diisopropylamine (7.31 g, 71.5 mmol) and tetrahydrofuran (22 g) then chilled to less than −15° C. (internal temperature). Hexyllithium (2.25 M in hexane: 21.8 g, 68.5 mmol) was carefully charged to the addition funnel. The hexyllithium solution was added through the addition funnel over 45 minutes with a maximum internal temperature of −17° C. The reaction was mixed for 1 hour at an internal temperature of approximately −15° C. to 0° C. The flask was equipped with another addition funnel and the toluene solution obtained from Example 7 (15.01 g, 58.33 mmol) was added through the addition funnel, followed by 4 g of tetrahydrofuran. The total addition time was 1 hour 45 minutes with a maximum internal temperature of −15° C. The solution was stirred at about −20° C. for 30 minutes. The flask was equipped with an addition funnel, which was charged with methyl iodide (9.3 g, 64-64 mmol) and tetrahydrofuran (3 g); this solution was added to the reaction mixture over 30 minutes, maintaining the internal temperature at no more than −15° C. After 30 minutes, the reaction was quenched into a chilled (~5° C.) 2M HCl solution (prepared from 31 mL, water and 8 g of concentrated HCl) while maintaining the temperature below 10° C. The reaction flask was rinsed with toluene (10 mL), which was added to the quench flask. The mixture was transferred to a separatory funnel and the layers were separated. The organic layer was rinsed with 17% NaCl solution (prepared by dissolving 2.5 g of NaCl in 15 g water). The tetrahydrofuran/toluene solution was used directly in the next step.

Example 9 tert-butyl 4-(aminocarbonyl)-4-methylpiperidine-1-carboxylate

A 500-mL flask equipped with an $N_2$ inlet/temperature probe, overhead stirrer and an addition funnel was charged with sodium amide (13.3 g, 327.3 mmol) and tetrahydrofuran (110 g) then warmed to 35° C. Through the addition funnel was slowly charged the tetrahydrofuran/toluene solution of Example 8 (35.57 g, 130.9 mmol). The addition funnel was rinsed with tetrahydrofuran (12 g). The reaction temperature was adjusted to 50° C. and the reaction was stirred for 3 hours before an HPLC sample was taken that showed the reaction was complete. In a separate flask equipped with an overhead stirred and a thermocouple was charged water (142 g), acetic acid (31.5 g) and toluene (54 g). The resulting mixture was then chilled to 0° C. The heterogeneous reaction mixture was quenched by addition to the acetic acid/toluene mixture while maintaining the temperature below 25° C. The reaction flask was rinsed with toluene (14 g) and water (14 g), which were added to the quench flask. The pH of the quench mixture was 6.04. The pH of the mixture was adjusted to 7.5 using 50% NaOH solution (11 g). The aqueous layer was extracted with 1:1 toluene/tetrahydrofuran (50 g). The organic layers were combined, filtered through a fritted glass filter and concentrated to a total volume of about 75 mL. The residue was diluted with toluene (125 g) and concentrated to a total volume of about 100 mL. Solid had formed during the distillations. The mixture was cooled to 0° C. and stirred for 1 hour. The mixture was filtered and the solid was washed with three portions of cold toluene and dried under vacuum to give the title compound. $^1$H NMR (400 MHz, CDCl$_3$) δ ppm 1.23 (s, 3H) 1.37-1.51 (m, 2H) 1.44 (s, 9H) 1.88-1.98 (m, 2H) 3.19-3.32 (m, 2H) 3.51-3.68 (m, 2H) 5.56-5.76 (m, 2H).

Example 10

4-methylpiperidine-4-carboxamide

A 500-mL three-neck round bottom flask was equipped with an overhead mechanical paddle stirrer, thermocouple with $N_2$-inlet, and reflux condenser that was vented to the atmosphere. The reactor was charged with the product of Example 9 (45.68 g, 188.5 mmol), p-toluenesulfonic acid monohydrate (46.67 g, 2453 mmol, 1.3 equiv) and isopropanol (179.2 g). The mixture was warmed to 80±10° C. After 45 minutes, the reaction solution was allowed to slowly cool; at about 78° C. the p-toluenesulfonate salt of the title compound began to precipitate from the reaction mixture. When the mixture had reached 70° C., heptane (40.2 g) was added to the mixture, which was then stirred for about 30 minutes. The mixture was then allowed to cool to ambient temperature over about 3 hours. The suspension was filtered and the reactor and cake were rinsed with a mixture of isopropanol (90.2 g) and heptane (78.7 g). The cake was dried under vacuum (~100 mmHg w/$N_2$ bleed) at a temperature of about 55-60° C. to give the p-toluenesulfonate salt of the title compound $^1$H NMR (400 MHz, DMSO-d$_6$) δ ppm 1.11 (s, 3H) 1.39-1.55 (m, 2H) 2.08 (d, J=14.55 Hz, 2H) 2.28 (s, 3H) 276-2.89 (m, 2H) 3.07-3.19 (m, 2H) 7.04 (s, 1H) 7.09-7.14 (m, 2H) 7.33 (s, 1H) 7.45-7.51 (m, 2H) 8.30 (s, 2H).

Example 11 tert-butyl 2-[4-(aminocarbonyl)-4-methylpiperidin-1-yl]isonicotinate

A 500-mL, 3-neck flask was charged with the product obtained from Example 10 (34.4 g, 109.4 mmol), K$_2$CO$_3$ (325 mesh, 35.3 g, 255.1 mmol) and a dimethyl sulfoxide/toluene solution of Example 5 (27.8 g of a 56.1 wt % solution, 72.9 mmol). The mixtures were stirred at 100° C. for about 36 hours. The mixture was cooled to room temperature and water (220 g) was added, slowly at first. The addition of water caused the product to precipitate out of solution. After stirring for about 1 hour, the mixture was filtered and the solid was washed with water and dried under vacuum to give the title compound. $^1$H NMR (400 MHz, CDCl$_3$) δ ppm 1.28 (s, 3H) 1.53-1.63 (m, 2H) 1.58 (s, 9H) 2.03-2.11 (m, 2H) 3.42-3.51 (m, 2H) 3.78-3.86 (m, 2H) 5.41-5.69 (m, 2H) 7.03 (dd, J=5.08, 1.24 Hz, 1H) 7.18 (s, 1H) 8.22 (dd, J=5.15, 0.75 Hz, 1H).

Example 12

4-methylpiperidin-4-amine

Step A

A 3-L 3-neck flask equipped with a mechanical stirrer and temperature probe was charged with the product of Example 9 (110.0 g, 0.454 mol), CH$_3$CN (260 g), and water (990 g). The resulting slurry was cooled to 10° C. and potassium hydroxide (130.6 g, 2.044 mol) was added, resulting in an exotherm from 10° C. to 24° C. The slurry was cooled to 1° C. and 1,3-dibromo-5,5-dimethylhydantoin (71.4 g, 0.250 mol) was added in one portion, resulting in an exotherm from 1° C. to 3° C. After 30 minutes the reaction was warmed to 23° C. After stirring for 1-hour sodium sulfite (5.5 g, 44 mmol) was added and the reaction stirred for 15 minutes. Ethyl acetate (496 g) was added and the reaction cooled to 11° C. K$_3$PO$_4$ (110.0 g, 0.518 mol) was added, resulting in a slight exotherm. The mixture was warmed to 23° C., transferred to a separatory funnel, and the layers were separated. The organic layer was washed once with a 25% aqueous sodium chloride solution. The organic layer was distilled to an oil, which was dissolved in methanol (500 mL) and distilled back to an oil. The oil was dissolved in methanol (740 mL) and held for use in the next reaction.

Step B

A 2-L, 3-neck flask equipped with a mechanical stirrer and temperature probe was charged with p-toluenesulfonic acid monohydrate (197.0 g, 1.036 mol) and isopropanol (290 g). The solution was heated to 60° C. The methanol solution from step A was added over 30 minutes, during which time the product crystallized from solution. The resulting slurry was stirred for 19 hours, cooled to 0° C., stirred for 1 hour, and filtered. The wet cake was washed twice with isopropanol (145 g) and the wet cake was dried for 24 hours at 50° C. and 20 mm Hg to give the di-p-toluenesulfonate salt of the title compound (92.2% yield over the two steps). $^1$H NMR (400 MHz, DMSO-d6) δ ppm 1.33 (s, 3H) 1.77-1.91 (m, 4H) 2.29 (s, 6H) 3.03-3.14 (m, 2H) 3.18-3.27 (m, 2H) 3.33 (br s, 2H) 7.08-7.15 (m, 4H) 7.44-7.52 (m, 4H) 8.04-8.43 (br s, 3H).

Example 13 tert-butyl 2-(4-amino-4-methylpiperidin-1-yl)-6-chloroisonicotinate

To a 500-mL flask equipped with an overhead stirrer and a nitrogen inlet was charged the product of Example 6 (10.0 g, 40.3 mmol) and the product of Example 12 (19.4 g, 42.3 mmol) followed by 1-methyl-2-pyrrolidinone (40 g). To the well-stirred reaction mixture was added $K_3PO_4$ (18.0 g, 84.6 mmol) and the mixture was warmed to 80° C. for 16 hours. An additional portion of $K_3PO_4$ (0.92 g, 2.0 mmol) was charged to the reaction mixture and the mixture was stirred for an additional 6-hour period. After cooling the reaction mixture to ambient temperature, methyl tert-butyl ether (65 mL) and a solution of $K_3PO_4$ (12.8 g) in water (130 mL) were added. After mixing and settling, 3 layers were present. The bottom two layers were separated and extracted with methyl tert-butyl ether (65 mL). The combined methyl tert-butyl ether layers were washed with a solution of $K_3PO_4$ (4.3 g) in water (100 mL). To the methyl tert-butyl ether layer was added 1-methyl-2-pyrrolidinone (28 mL) and the solution was concentrated under vacuum to remove methyl tert-butyl ether. The 1-methyl-2-pyrrolidinone solution of the title compound was used in the next step.

Example 14 tert-butyl 2-(4-amino-4-methylpiperidin-1-yl)isonicotinate

Method A

A 1-L, 3-neck flask equipped with a mechanical stirrer and temperature probe was charged with the product of Example 11 (49.00 g, 0.153 mol) and tetrabutylammonium bromide (TBAB, 49.46 g, 0.153 mol). Tetrahydrofuran (132 g) was added and the resulting slurry was cooled to 5° C. A 4M Sodium hydroxide solution (393 g) was added and the slurry was cooled to less than 0° C. 1,3-Dibromo-5,5-dimethylhydantoin (DBDMH, 24.13 g, 0.0844 mol) was added in 4 portions over 15 minutes, resulting in an exotherm from 2.2° C. to 1.6° C. The reaction was stirred for 90 minutes A 2-L flask was charged with 6M HCl (294 g methyl tert-butyl ether (91 g), and $Na_2SO_3$ (19.6 g) and the solution was cooled to 10° C. The reaction mixture was transferred into the quench solution, which resulted in an exotherm to 20° C. and the evolution of carbon dioxide gas. The reaction flask was rinsed with methyl tert-butyl ether (91 g), which was added to the quench solution. The quenched reaction solution had a pH of approximately 3 as determined by pH paper. After stirring for 5 minutes, 4M sodium hydroxide (196 g) was charged to the quenched reaction solution resulting in an exotherm to 20° C. The quenched reaction solution had a pH of approximately 12 as determined by pH paper. After transferring to a separatory funnel, the layers were separated and the aqueous layer was back extracted with methyl tert-butyl ether. The combined organic layers were washed with a brine-sulfite solution (prepared from 12.3 g $Na_2SO_3$, 24.5 g NaCl, and 208 g water). The combined organic layers were distilled to an oil, which was reconstituted in 1-methyl-2-pyrrolidinone (1-methyl-2-pyrrolidinone, 75 mL) and distilled to remove methyl tert-butyl ether. The 1-methyl-2-pyrrolidinone solution of product was assayed at 38.91 g (87.3% yield).

Method B

To a Parr hydrogenation vessel under a nitrogen atmosphere was charged 5% Pd/Al$_2$O$_3$ (1.02 g, 10 wt % load) and $K_3PO_4$ (6.92 g, 1.05 equiv) followed by the 1-methyl-2-pyrrolidinone solution from Example 13 (31.4 g of a 31 wt % solution, 29.9 mmol). The vessel was sealed and sparged with hydrogen and then warmed to 40° C. with shaking. After 4 hours, the vessel was sparged with nitrogen, cooled to ambient temperature and filtered. The catalyst and solids were rinsed with 1-methyl-2-pyrrolidinone (2×10 g). The crude solution was used in the next step.

Example 15

4-[2-[(2S,5R)-2-Cyano-5-ethynyl-pyrrolidin-1-yl]-2-oxo-ethylamino]-4-methyl-3,4,5,6-tetrahydro-2H-[1, 2']bipyridinyl-4'-carboxylic acid tert-butyl ester; D-tartaric acid salt A 500-mL flask with nitrogen inlet, a temperature probe and a mechanical stirrer was charged the product of Example 14 in 1-methyl-2-pyrrolidinone (56.4 g of a 31.4% wt solution, 61 mmol) followed by milled $K_3PO_4$ (19.2 g, 90.8 mmol) and potassium iodide (1.0 g, 6.1 mmol). The slurry was degassed by nitrogen sparging for 10 min, then the solution was warmed to 35° C. The product of Example 4 (12.55 g, 63.8 mmol) was dissolved in 1-methyl-2-pyrrolidinone (20 g) and added portion wise over 30 minutes maintaining the internal temperature between 35° C. and 40° C. After 4 hours, methyl tert-butyl ether (263 mL) and water (206 mL) were charged and the pleases were separated. The methyl tert-butyl ether layer was sequentially washed with 5% wt $KH_2PO_4$ (208 g) then water (206 mL). The methyl tert-butyl ether layer was filtered though a Cuno R53SP carbon filter, rinsing with a small amount of methyl tert-butyl ether. The methyl tert-butyl ether was distilled to approximately 160 mL. As the distillation continued, isopropanol (395 mL) was added to maintain the solvent level around 160 mL. The resulting isopropanol solution was warmed to 60° C., and then D-tartaric acid (9.1 g, 60.6 mmol) was charged and the solution was stirred for 15 minutes at 60° C. After nucleation occurred, the slurry was cooled to ambient temperature over 30 minutes, filtered and washed with isopropanol (2×90 mL). The cake was dried under vacuum at 50° C. with a nitrogen bleed to give the D-tartrate salt of the title compound. $^1$H NMR (400 MHz, DMSO-d6) δ ppm 1.20 (s, 3H) 1.53 (s, 9H) 1.55-1.74 (m, 4H) 2.07-2.16 (m, 1H) 2.17-2.43 (m, 3H) 3.33-3.45 (m, 2H) 3.61 (d, J=2.20 Hz, 1H) 3.73-3.87 (m, 3H) 4.12 (s, 2H) 4.77 (t, J=7.00 Hz, 1H) 4.91-4.98 (m, 1H) 6.94 (dd, J=5.08, 1.10 Hz, 1H) 7.14 (s, 1H) 8.21 (d, J=5.08 Hz, 1H).

Example 16

4-[2-[(2S,5R)-2-Cyano-5-ethynyl]-pyrrolidin-1-yl]-2-oxo-ethylamino-4-methyl-3,4,5,6-tetrahydro-2H-[1,2']bipyridinyl-4'-carboxylic acid A 1-L cylindrical jacketed flask equipped with an overhead mechanical stirrer, a programmable syringe pump, N$_2$-inlet and temperature probe was charged with the product of Example 15 (102.19 g, 0.170 mol), distilled water (1022 g), and 85% phosphoric acid (58.85 g, 0.509 mol). The slurry was heated to 60° C. and held at this temperature for 16 hours to drive the reaction to completion. The reaction mixture became practically cleat as it reached the target temperature and remained homogeneous for most of the reaction. Once complete, the reaction was cooled to room temperature, filtered through a carbon cartridge (Cuno R53SP, 0.9 g carbon/pad, previously rinsed with 200 mL of water), and filtered through #1 Whatman paper filter. A 102-mL water rinse was employed to minimize product losses in the filters and was combined with the filtrate.

The product was crystallized at room temperature as a zwitterion by neutralizing the clear filtrate. A solution of sodium hydroxide (501.85 g solution, 8.77 wt % NaOH) was added over 30 min with a syringe pump to adjust the pH to 4.5 to 5.0. The solution was allowed to crystallize, and the addition was continued to a pH between 6.0 and 7.0. The slurry was cooled to 10° C., stirred for 1 hour and filtered, and washed with two separate 255-mL portions of water. The procedure gave 100 g of white solid that was 60.9 wt % pure by HPLC (91% yield). The zwitterion was carried on to the next step as a wetcake. $^1$H NMR (400 MHz, Acetic Acid-d$_4$) δ ppm 1.65 (s, 2H) 2.09-2.22 (m, 2H) 2.22-2.37 (m, 3H) 2.37-2.54 (m, 3H) 3.01 (d, J=2.06 Hz, 1H) 3.46 (t, J=11.60 Hz, 2H) 4.13-4.36 (m, 3H) 4.38-4.53 (t, 1H) 4.78-4.86 (m, 1H) 4.86-4.94 (m, 1H) 7.30 (dd, J=6.17, 0.96 Hz, 1H) 7.64 (s, 1H) 8.11 (d, J=6.18 Hz, 1H).

Example 17

4-[2-[(2S,5R)-2-Cyano-5-ethynyl-pyrrolidin-1-yl]-2-oxo-ethylamino]-4-methyl-3,4,5,6-tetrahydro-2H-[1,2']bipyridinyl-4'-carboxylic acid; L-malic acid salt A 1-L round bottom flask was charged with the zwitterion wetcake from Example 16 (99.58 g at 60.9 wt %, 0.153 mol), 389 g of distilled water, 315 g of ethanol and 23.19 g (0.173 mol) of L-malic acid. The slurry was heated in a 70° C. water bath to achieve dissolution. The clear solution was filtered though a #1 Whatman paper and transferred into a 1-L cylindrical jacketed flask preheated to 40° C. and equipped with an overhead mechanical stirrer, a distillation/reflux condenser, N$_2$-inlet, and temperature probe. 53.99 g of 1:1 ethanol/water solution was used to rinse the round bottom flask, filter, and filtration flask and was combined with the product filtrate. The clear solution was cooled over two hours to 20° C., and allowed to crystallize overnight. The thin slurry was distilled under reduced pressure (~77-87 mm Hg at 40° C.) to approximately 450 mL, and further chased twice with ethanol: the first chase with 421 g of ethanol to a volume of 370 mL, and a second chase with 425 g of ethanol to a volume of 370 mL. Water (36.7 g) and ethanol (57.2 g) were added. In order to minimize losses from product build-up on the reactor wall during the distillation, the slurry is heated to 40° C., held for two hours, cooled to 0° C. over 4 hours, and held overnight. The product slurry was filtered and washed with 300 mL of cold ethanol. Product was dried overnight at 50° C. under reduced pressure to yield L-malate salt of the title compound. $^1$H NMR (400 MHz, DMSO-d6) δ ppm 1.26 (s, 3H) 1.56-1.79 (m, 4H) 1.96-2.17 (m, 1H) 2.17-2.46 (m, 4H) 2.56 (dd, J=15.64, 7.14 Hz, 1H) 3.23-3.38 (m, 2H) 3.51-3.75 (m, 2H) 3.82-3.99 (m, 3H) 4.08 (dd, J=7.14, 6.17 Hz, 1H) 4.62-4.83 (m, 1H) 4.91-5.26 (m, 1H) 699 (dd, J=5.01, 1.03 Hz, 1H) 7.20 (s, 1H) 8.20 (d, J=5.08 Hz, 1H) 8.62-10.82 (br m, 4H).

Example 18

(2S,5S) 2-tert-Butoxycarbonylamino-5-hydroxy-7-trimethylsilanyl-hept-6-ynoic acid methyl ester A 50-L flask was charged with the product from Example 1 (2.4.3 kg, 7.11 mol) and isopropanol (29 L). The solution was sparged with dry argon gas for about 50 minutes and the reaction was run under an argon atmosphere. [(1S,2S)—N-(p-toluenesulfonyl)-1,2-diphenylethanediamine](p-cymene)ruthenium (I) (Kanto Chemical Co. Inc. Catalog #41067-95, CAS#188444-42-0, 21.31 g, 0.036 mol) was added under positive argon. The reaction was followed by HPLC and additional charges of catalyst were made (21.31 g, 0.036 mol at 6 hours and 8.27 g, 0.014 mol at 8 hours) and the mixture was stirred at room temperature overnight. After a total of 22 hours, the reaction was complete. The reaction was concentrated and isopropyl acetate was added and the concentration was continued to completely replace the alcohol solvent. The final solution was distilled to about 9 L. Heptane (20 L) was added and the mixture was stirred at room temperature for 30 minutes and at 0° C. for 1 hour. The solid was collected by filtration and the solid was washed with cold heptane (2×4 L) and dried in a vacuum oven at 35-40° C. The procedure gave 2.27 kg (91.5% yield) of white solid. $^1$H NMR (400 MHz, CDCl$_3$) δ ppm 0.16 (s, 9H) 1.44 (s, 9H) 1.66-1.86 (m, 3H) 1.93-2.06 (m, 1H) 2.18 (d, J=4.67 Hz, 1H) 3.73 (s, 3H) 4.29-4.43 (m, 2H) 5.11 (d, J=7.41 Hz, 1H) $^{13}$C NMR (101 MHz, CDCl$_3$) δ ppm 0.24, 28.56, 28.62, 33.42, 52.46, 53.14, 62.14, 79.97, 89.84, 105.77, 116.39, 154.97, 172.55.

Example 19

(2S,5S)-5-Trimethylsilanylethynyl-pyrrolidine-2-carboxylic acid methyl ester

A 100-L, flask equipped with an overhead stirrer, a thermocouple and an addition funnel was charge with the product from Example 18 (2.1 kg, 6.08 mol), CH$_2$Cl$_2$ (32 L) and triethylamine (0.92 kg, 9.12 mol) and the solution was cooled to 0° C. Methanesulfonyl chloride (0.77 kg, 6.69 mol) was added through the addition funnel such that the internal temperature of the reaction remained below 5° C. The reaction was followed by HPLC until the starting material was consumed. 4 M HCl in dioxane (23 L, 91.2 mol) was added through the addition funnel such that the temperature remained below 10° C. The ice bath was removed and the solution was allowed to stir at room temperature for 2 hours. The reaction was concentrated to about 5 L. Dioxane (4 L) was added and the solution was concentrated to about 4 L. Tetrahydrofuran (27 L) was added followed by solid K$_2$CO$_3$ (2.1 kg, 15.2 mol). After stirring for 30 minutes, the reaction was cooled to 0° C. and water (18 L) was added such that the temperature remained below 15° C. After 20 minutes, the layers were separated. The aqueous layer was extracted with tert-butyl methyl ether (12 L). The combined organic layers contained 1.37 kg of product (99.9% yield) and were used directly in the next reaction.

Example 20

(2S,5S)-1-(2-Chloroacetyl)-5-ethynyl-pyrrolidine-2-carboxylic acid

A solution of the product from Example 19 (11.9 kg total, 308.1 g active, 1.37 mol) was concentrated to about 1240 grams and transferred to a 5-L flask. Tetrahydrofuran (1800 mL) was added and the mixture was cooled to less than 10° C. LiOH—H$_2$O (127 g, 3.03 mol) was added over 5 minutes. After 1 hour the mixture was cooled to 0° C. and chloroacetyl chloride (339.8 g, 3.01 mol) was added over about 60 minutes. After 1.5 hours, the reaction was quenched by the addition of a 1/9 mixture of 6 M HCl and 25% aq NaCl (1.8 kg) and isopropyl acetate (1.9 L). The layers were separated and the organic layer was washed with a 1/9 mixture of 6 M HCl and 25% aq NaCl (1.1 kg). The combined aqueous layers were extracted with isopropyl acetate (2×2 L). The combined organic layers were concentrated several times from isopropyl acetate to dry and then to about 800 grams total weight. Solids had come out of solution during the concentration. Heptane (200 mL) was added slowly, causing more solid to precipitate. After stirring for 2-3 h, the mixture was filtered and the solids were washed with 1:1 isopropyl acetate/heptane (250 mL) and dried at 40° C. in a vacuum oven to give 255 g (86% yield) of white solid. The $^1$H NMR spectrum of the product exhibited 2 rotomers. Rotomer (a) was the major rotomer and rotomer (U) was the minor rotomer. $^1$H NMR (400 MHz, DMSO-d$_6$) δ ppm 1.78-2.07 (m, 2H) 2.08-2.30 (m, 2H) rotomer b: 3.13 (d, J=2.20 Hz, 1H) rotomer a: 3.46 (d, J=2.20 Hz, 1H) rotomer b: 4.09 (d, J=14.13 Hz, 1H) rotomer a: 4.32 (d, J=14.41 Hz, 1H) 4.21 (t, J=741 Hz, 7H) rotomer b; 4.40 (d, J=14.00 Hz, 1H) rotomer a: 4.59 (d, J=14.27 Hz, 1H) rotomer b; 4.61-467 (m, 1H) rotomer a: 4.77-4.85 (m, 1H) 12.53-12.85 (m, 1H)

Example 21

(2S,5S)-1-(2-Chloroacetyl)-5-ethynyl-pyrrolidine-2-carbonitrile

Step A:
A 5-L flask, equipped with an overhead mechanical stirrer and N$_2$ line and an addition funnel, was charged with the product from Example 20 (200 g, 930 mmol) and tetrahydrofuran (3 L). The solution was cooled to −10° C. and N-methylmorpholine (130 mL, 1163 mmol) was added all at once. Isobutyl chloroformate (148 mL, 1116 mmol) was added by addition funnel over 20-30 minutes. After stirring for 1.5 hours, ammonia gas (32 g, 1860 mmol) was bubbled into the solution over a 3-hour period. The precipitated solids were removed by filtration and the solid was washed with tetrahydrofuran. The filtrate was assayed and contained 178 g product (90% yield) and was used directly in the next step.

Step B:
A 5-L flask, equipped with an overhead mechanical stirrer and N$_2$ line and an addition funnel was charged with tetrahydrofuran (800 mL) and N,N-dimethylformamide (172 mL, 2232 mmol) and the solution was cooled to 0° C. Thionyl chloride (156 mL, 2139 mmol) was added over about 1 h and the resulting solution was stirred for about 2 hours. The amide solution from Step A was added over about 1 hour and the mixture was stirred for 30 minutes. 1 M K$_2$HPO$_{41}$ solution (1500 mL) was added slowly followed by toluene (1500 mL). The mixture was concentrated to remove tetrahydrofuran and the resulting layers were separated. The aqueous layer was extracted with toluene (2×1000 mL). The combined organic layers were washed with 25% NaCl solution (2×1600 mL, 1×600 mL). The organic layer was filtered and concentrated to a total weight of about 400 g and seeds were added. After stirring for 72 hours at room temperature, heptane (300 mL) was added slowly and the mixture was stirred for 2 hours. The mixture was filtered and the solid was washed with 1:1 toluene/heptane (200 mL) and dried in a vacuum oven at 40° C. overnight to give 128.3 g (70% yield). $^1$H NMR (400 MHz, CDCl$_3$) δ ppm 2.23-2.52 (m, 4H) 2.56 (d, J=1.78 Hz, 1H) 4.31 (dd, J=12.9, 66.8 2H) 467-494 (m, 2H).

It is understood that the foregoing detailed description and accompanying examples are merely illustrative and are not to be taken as limitations upon the scope of the invention, which is defined solely by the appended claims and their equivalents. Various changes and modifications including, hut not limited to, those relating to the chemical structures, substituents, derivatives, intermediates, syntheses, formulations and/or methods of use of the invention, can be made without departing from the spirit and scope thereof.

We claim:
1. A process for preparing the L-malic acid salt of a compound of formula (I),

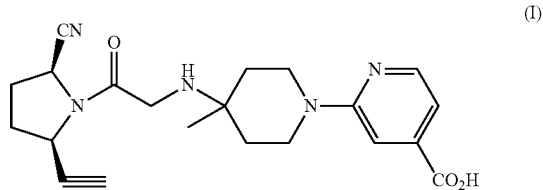 [SMILES: C#C[C@H]1CC[C@@H](C#N)N1C(=O)CNC1(C)CCN(c2cc(C(=O)O)ccn2)CC1]

comprising the steps of:
(a) treating a compound of formula (XVIII) wherein X$^2$ is Cl, Br, I, methanesulfonate or p-toluenesulfonate, with a compound of formula (XIX) or salts thereof wherein P$^1$ is an acid protecting group, potassium iodide, and milled potassium phosphate, in an aprotic organic solvent, to provide a compound of formula (XX)

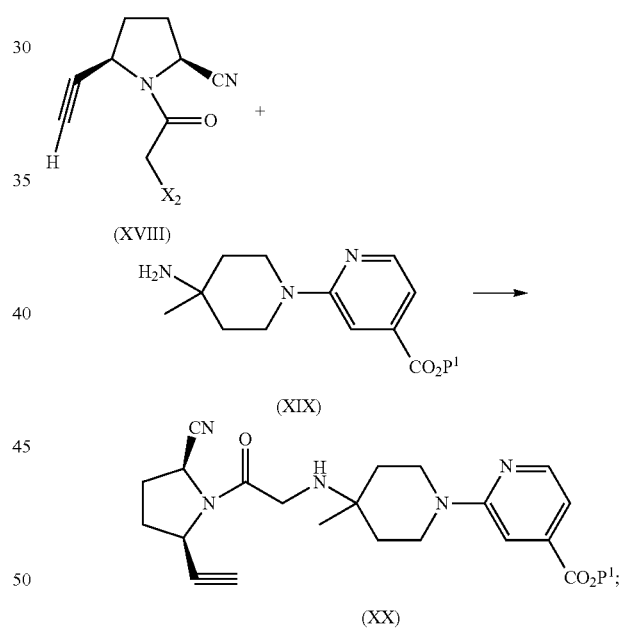

(b) treating the compound of formula (XX) with D-tartaric acid in a 1:1 ratio to provide the D-tartrate salt of the compound of formula (XX);
(c) deprotecting the D-tartrate salt of step (b) to provide a compound of formula (I); and
(d) treating an aqueous solution of the compound of formula (I) with a C$_{1-6}$ alcoholic solution of L-malic acid in a 1:1.1 ratio to form the L-malic acid salt of the compound of formula (I);
wherein the compound of formula (XVIII) is prepared by a process comprising:
(a)
(i) asymmetric reduction of a compound of formula to a compound of formula (XXXVII), wherein P$^2$ is an amine-protecting group, R[1] is an acid protecting group, and R[2] is $C_{1-6}$ alkyl

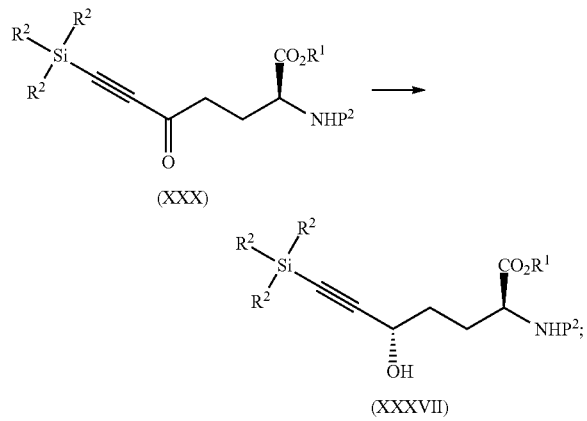

(ii) activating the compound of formula (XXXVII) to provide a compound of formula (XXXVIII), wherein R[4] is trihaloacetyl, methanesulfonyl, benzenesulfonyl or p-toluenesulfonyl

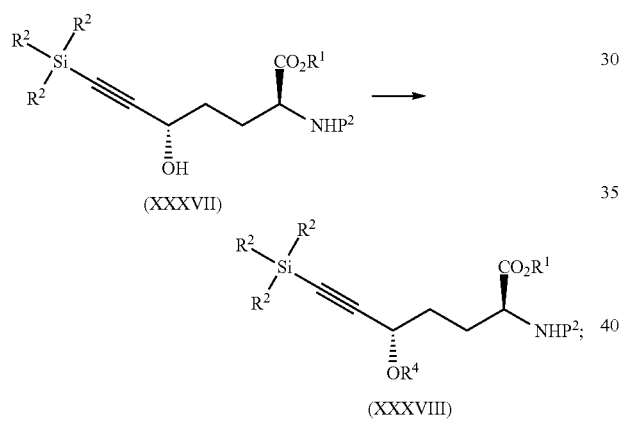

(iii) deprotecting and cyclizing the compound of formula (XXXVIII) to provide a compound of formula (XXXVI) or salt thereof

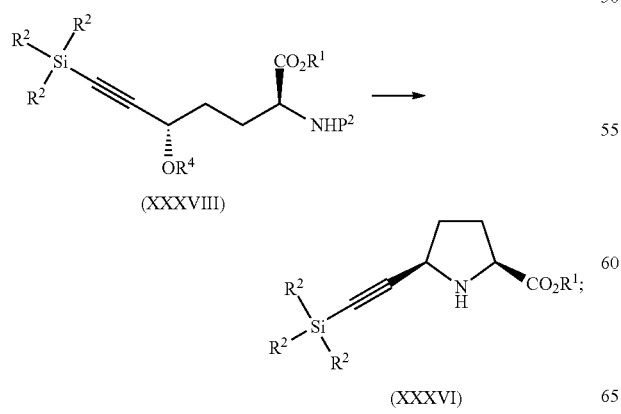

(iv) saponifying a compound of formula (XXXVI) or salts thereof to provide a compound of formula (XXXIX), wherein R[1] is an acid protecting group and R[2] is $C_{1-6}$ alkyl

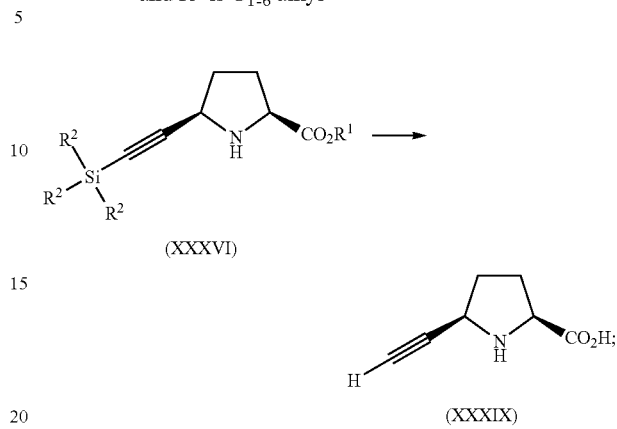

(v) treating the compound of formula (XXXIX) or salts thereof with a reagent having formula $X^2CH_2COY^2$ to provide a compound of formula (XL), wherein $X^2$ and $Y^2$ are independently Cl or Br

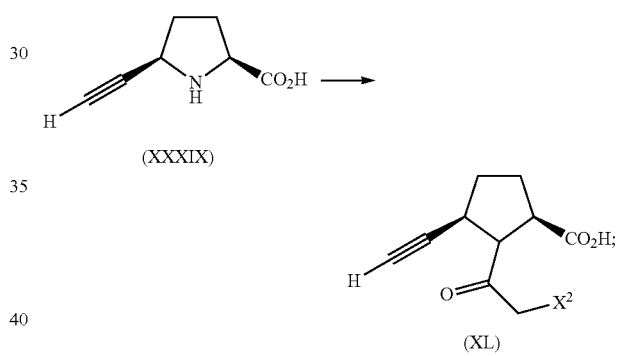

(vi) treating the compound of formula (XL) with ammonia in the presence of a coupling reagent and a base to provide a compound of formula (XLI)

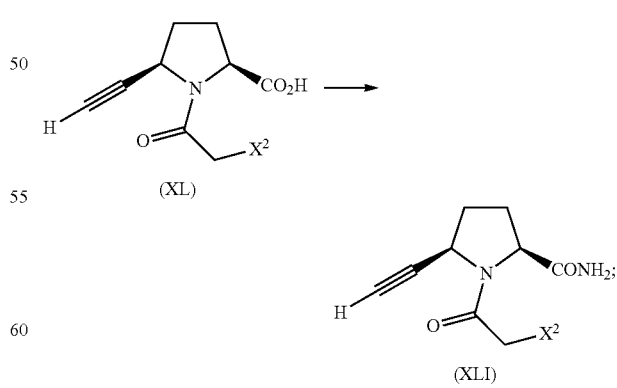

(vii) dehydrating the compound of formula (XLI) to provide a compound of formula (XVIII)

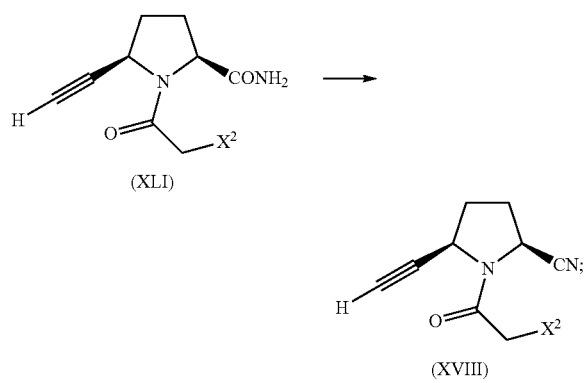

(XLI)

(XVIII)

or (b)

(i) treating the compound of formula (XXX) with an acid and a reducing agent, in a solvent, to provide a compound of formula (XXXI)

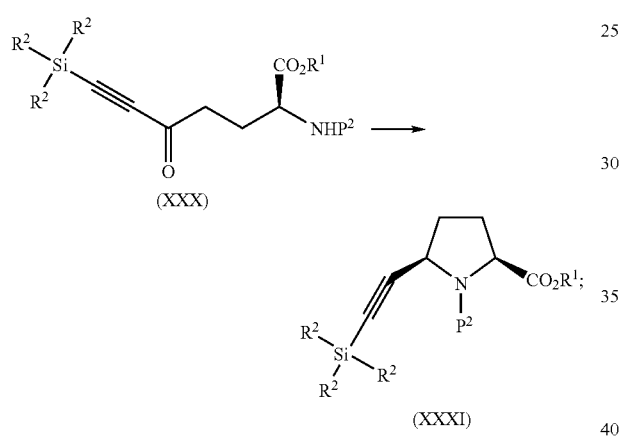

(XXX)

(XXXI)

(ii) treating the compound of formula (XXXI) with a base, followed by treatment with an acid, to provide a compound of formula (XXXII)

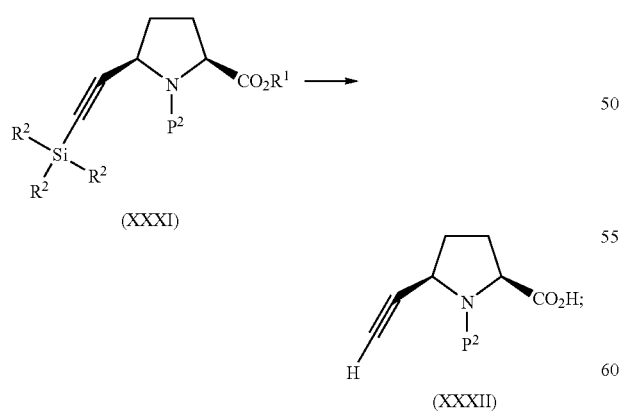

(XXXI)

(XXXII)

(iii) treating the compound of formula (XXXII) with ammonia in the presence of a coupling reagent and a base, to provide a compound of formula (XXXIII);

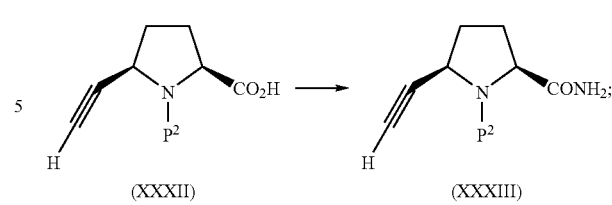

(XXXII)   (XXXIII)

(iv) treating the compound of formula (XXXIII) with a dehydrating agent to provide a compound of formula (XXXIV);

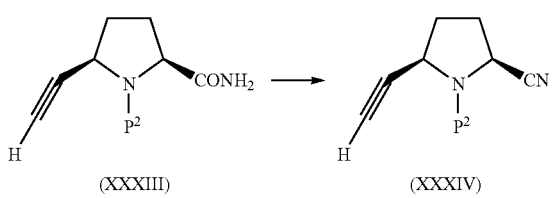

(XXXIII)   (XXXIV)

(v) deprotecting the compound of formula (XXXIV) to provide a compound of formula (XXXV) or salts thereof

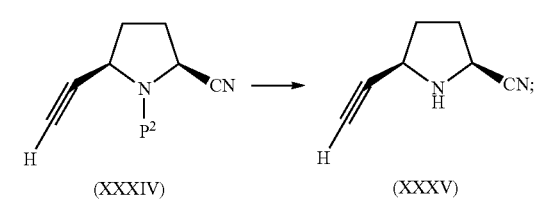

(XXXIV)   (XXXV)

and (vi) treating the compound of formula (XXXV) or salts thereof with a reagent having formula $X^2CH_2COY^2$ wherein $X^2$ and $Y^2$ are independently Cl or Br, to provide a compound of formula (XVIII)

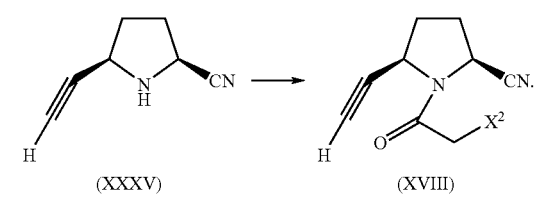

(XXXV)   (XVIII)

2. The process according to claim 1, wherein the compound of formula (XVIII) is prepared by a process comprising:

(a) asymmetric reduction of a compound of formula (XXX) to a compound of formula (XXXVII), wherein $P^2$ is an amine-protecting group, $R^1$ is an acid protecting group, and $R^2$ is $C_{1-6}$ alkyl

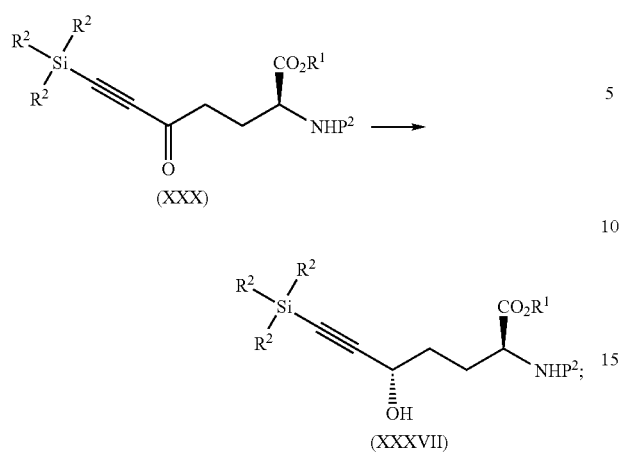

(b) activating the compound of formula (XXXVII) to provide a compound of formula (XXXVIII), wherein $R^4$ is trihaloacetyl, methanesulfonyl, benzenesulfonyl or p-toluenesulfonyl

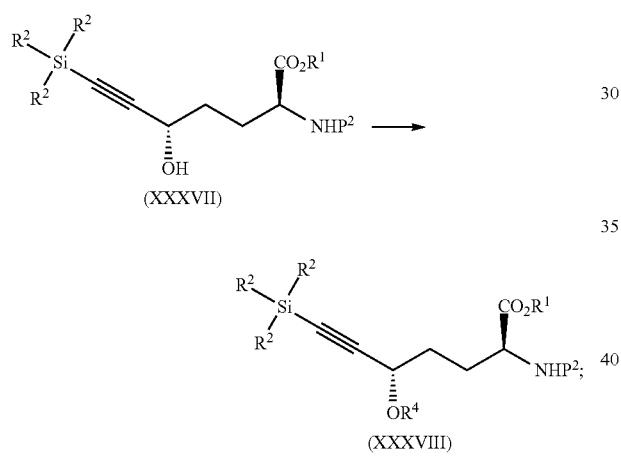

(c) deprotecting and cyclizing the compound of formula (XXXVIII) to provide a compound of formula (XXXVI) or salt thereof

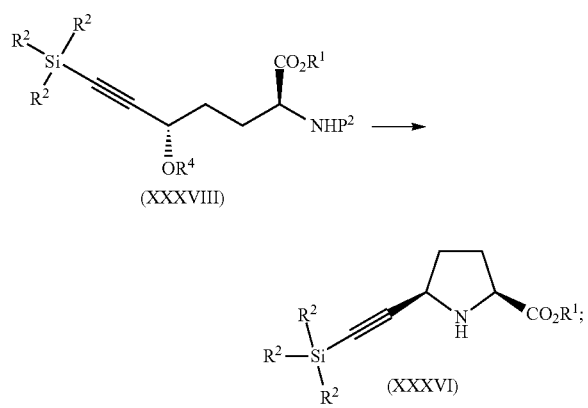

(d) saponifying a compound of formula (XXXVI) or salts thereof to provide a compound of formula (XXXIX), wherein $R^1$ is an acid protecting group and $R^2$ is $C_{1-6}$ alkyl

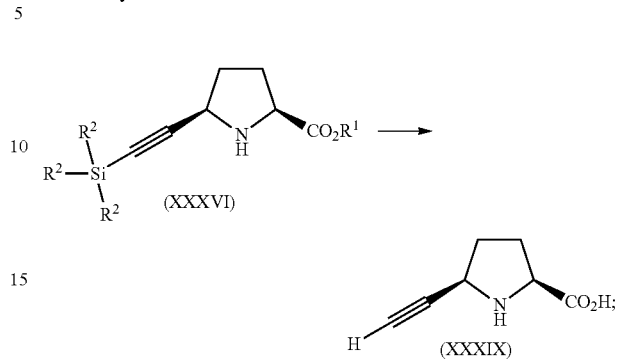

(e) treating the compound of formula (XXXIX) or salts thereof with a reagent having formula $X^2CH_2COY^2$ to provide a compound of formula (XL), wherein $X^2$ and $Y^2$ are independently Cl or Br

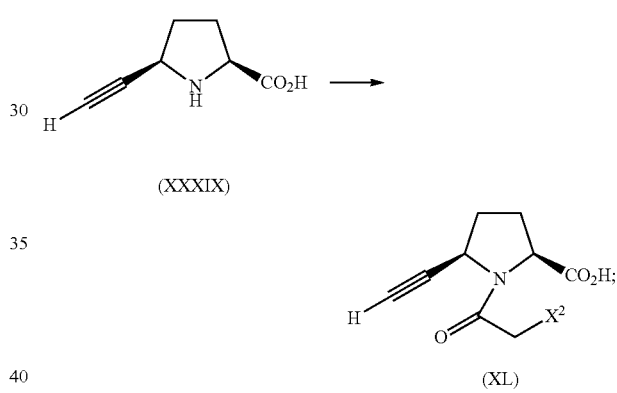

(f) treating the compound of formula (XL) with ammonia in the presence of a coupling reagent and a base to provide a compound of formula (XLI)

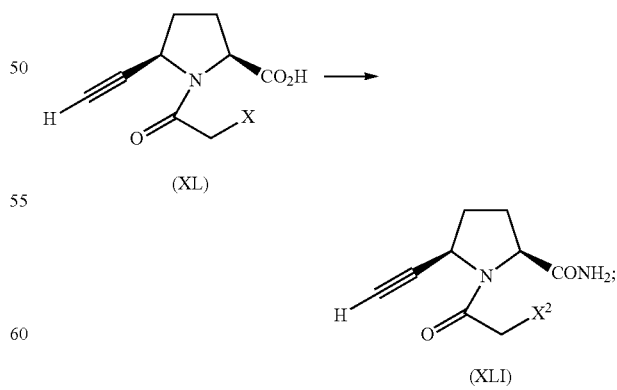

and (g) dehydrating the compound of formula (XLI) to provide a compound of formula (XVIII)

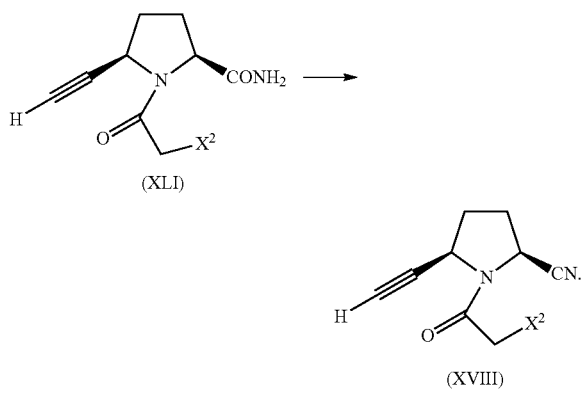

3. The process according to claim 1 wherein the solvent is selected from the group consisting of acetonitrile, lactams, N,N-dimethylamides of formic acid and aliphatic $C_{1-6}$ carboxylic acids, sulfoxides, ethers, aliphatic ketones, and mixtures thereof.

4. The process according to claim 1 wherein the solvent is selected from the group consisting of acetonitrile, 1-methyl-2-pyrrolidinone, N,N-dimethylformamide, N,N-dimethylacetamide, tetrahydrofuran, dioxane, and mixtures thereof.

5. The process according to claim 1 wherein an acid selected from the group consisting of trifluoroacetic acid, benzenesulfonic acid, p-toluenesulfonic acid, methanesulfonic acid, hydrogen chloride, and phosphoric acid is added in step (c).

6. The process according to claim 5 wherein the acid is phosphoric acid.

7. The process according to claim 1, wherein the compound of formula (XVIII) is prepared by a process comprising:

(a) treating the compound of formula (XXX) with an acid and a reducing agent, in a solvent, to provide a compound of formula (XXXI)

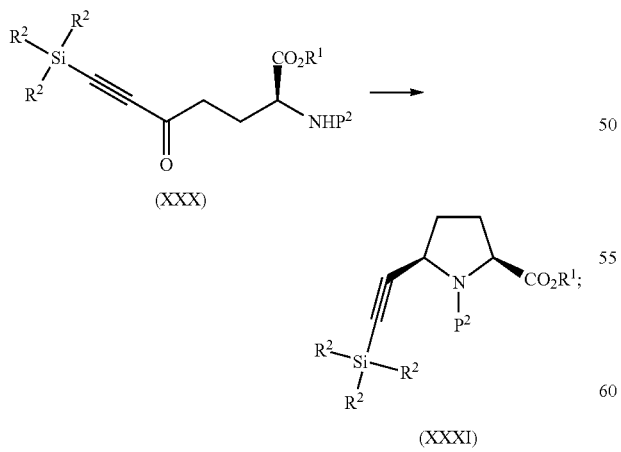

(b) treating the compound of formula (XXXI) with a base, followed by treatment with an acid, to provide a compound of formula (XXXII)

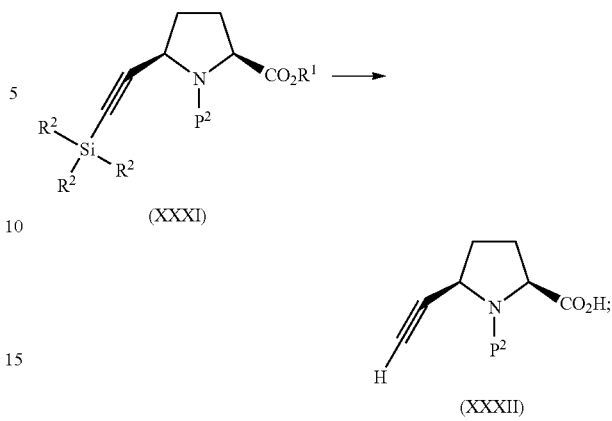

(c) treating the compound of formula (XXXII) with ammonia in the presence of a coupling reagent and a base, to provide a compound of formula (XXXIII)

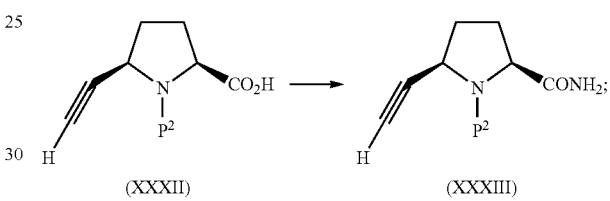

(d) treating the compound of formula (XXXIII) with a dehydrating agent to provide a compound of formula (XXXIV)

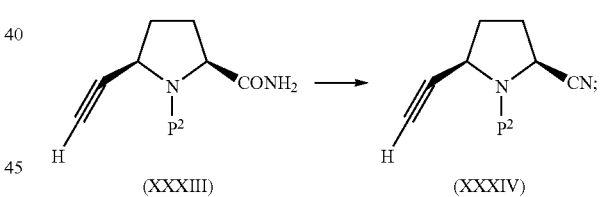

(e) deprotecting the compound of formula (XXXIV) to provide a compound of formula (XXXV) or salts thereof

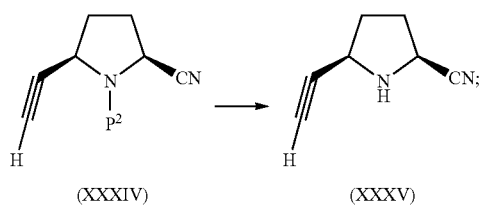

and (f) treating the compound of formula (XXXV) or salts thereof with a reagent having formula $X^2CH_2COY^2$ wherein $X^2$ and $Y^2$ are independently Cl or Br, to provide a compound of formula (XVIII)

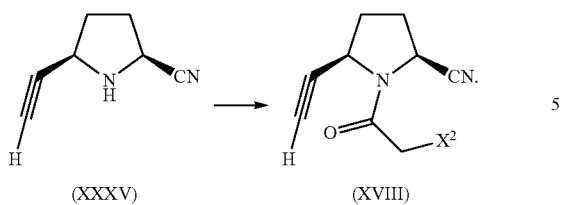
8. (2S,5R)-5-ethynyl-1-{N-(4-methyl-1-(4-carboxy-pyridin-2-yl)piperidin-4-yl)glycyl}pyrrolidine-2-carbonitrile, L-malic acid salt.
* * * * *